(12) United States Patent
Wang

(10) Patent No.: US 6,403,566 B1
(45) Date of Patent: Jun. 11, 2002

(54) NUCLEOSIDES HAVING BICYCLIC SUGAR MOIETY

(75) Inventor: Guangyi Wang, Irvine, CA (US)

(73) Assignee: ICN Pharmaceuticals, Inc., Costa Mesa, CA (US)

( * ) Notice: Subject to any disclaimer, the term of this patent is extended or adjusted under 35 U.S.C. 154(b) by 0 days.

(21) Appl. No.: 09/451,708

(22) Filed: Dec. 1, 1999

Related U.S. Application Data

(63) Continuation of application No. PCT/US99/11442, filed on May 24, 1999.
(60) Provisional application No. 60/086,719, filed on May 26, 1998.

(51) Int. Cl.[7] .................. A61K 31/70; C07H 19/20; C07H 19/10
(52) U.S. Cl. ................ 514/45; 514/46; 514/47; 514/48; 514/49; 514/50; 514/51; 536/26.7; 536/26.8
(58) Field of Search .................. 536/26.7, 26.8; 514/45, 46, 47, 48, 49, 50, 51

(56) References Cited

FOREIGN PATENT DOCUMENTS

WO    WO 99/14226    3/1999    ........... C07H/21/00

OTHER PUBLICATIONS

Obika et al., Tetrahedron Letters, vol. 38, No. 50, pp. 8735–8738 (1997).*

Altmann, K., et al. 4',6'–Methano Carbocyllic Thyidine: A Conformationally Constrained Building Block for Oligonucleotides. Tetrahedron Letters (1994), 35(15):2331–2334.

Hong, J.H., et al. Synthesis of Novel D–2',3'dideoxy–2',3' endo–methylene Nucleosides. Tetrahedron Letters (1998), 39: 225–228.

Obiks, S., et al. Synthesis of 3'–0,4'–C–Methyleneuridine and –cytidine. Novel bicyclic Nucleosides Having a Fixed $C_3$–endo Sugar Puckering. Tetrahedron Letters (1997), 38(50):8735–8738.

\* cited by examiner

*Primary Examiner*—James O. Wilson
(74) *Attorney, Agent, or Firm*—Rutan & Tucker, LLP; Robert D. Fish

(57) ABSTRACT

Conformationally restricted 2', 4'—bridged nucleoside analogues are described herein. The compounds can be prepared by cyclization at C2' and C4' of nucleosides through a linker or linking molecule. These novel nucleosides have a desired, locked sugar pucker and are potentially useful as pharmaceutical ingredients. Oligonucleotides composed of these novel nucleosides are useful for oligonucleotide therapeutic and diagnostic compounds.

8 Claims, No Drawings

SEQUENCE LISTING

<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:modified_base
<220> FEATURE:
<221> NAME/KEY: modified_base
<222> LOCATION: (4)
<223> OTHER INFORMATION: 2',4'-C-bridged thymid ine
<220> FEATURE:
<221> NAME/KEY: modified_base
<222> LOCATION: (6)
<223> OTHER INFORMATION: 2',4'-C-bridged thymid ine
<220> FEATURE:
<221> NAME/KEY: modified_base

```
<222> LOCATION: (11)
<223> OTHER INFORMATION: 2',4'-C-bridged thymid ine
<220> FEATURE:
<221> NAME/KEY: modified_base
<222> LOCATION: (12)
<223> OTHER INFORMATION: 2',4'-C-bridged thymid ine
<220> FEATURE:
<221> NAME/KEY: modified_base
<222> LOCATION: (15)
<223> OTHER INFORMATION: 2',4'-C-bridged thymid ine

<400> SEQUENCE: 1
atctctccgc ttcctttc                                                18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial  Sequence:modified_
      base
<220> FEATURE:
<221> NAME/KEY: modified_base
<222> LOCATION: (2)
<223> OTHER INFORMATION: 2',4'-C-bridged thymid ine
<220> FEATURE:
<221> NAME/KEY: modified_base
<222> LOCATION: (4)
<223> OTHER INFORMATION: 2',4'-C-bridged thymid ine
<220> FEATURE:
<221> NAME/KEY: modified_base
<222> LOCATION: (6)
<223> OTHER INFORMATION: 2',4'-C-bridged thymid ine
<220> FEATURE:
<221> NAME/KEY: modified_base
<222> LOCATION: (11)
<223> OTHER INFORMATION: 2',4'-C-bridged thymid ine
<220> FEATURE:
<221> NAME/KEY: modified_base
<222> LOCATION: (12)
<223> OTHER INFORMATION: 2',4'-C-bridged thymid ine
<220> FEATURE:
<221> NAME/KEY: modified_base
<222> LOCATION: (15)
<223> OTHER INFORMATION: 2',4'-C-bridged thymid ine
<220> FEATURE:
<221> NAME/KEY: modified_base
<222> LOCATION: (16)
<223> OTHER INFORMATION: 2',4'-C-bridged thymid ine
<220> FEATURE:
<221> NAME/KEY: modified_base
<222> LOCATION: (17)
<223> OTHER INFORMATION: 2',4'-C-bridged thymid ine

<400> SEQUENCE: 2
atctctccgc ttcctttc                                                18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial  Sequence:modified_
      base
<220> FEATURE:
<221> NAME/KEY: modified_base
<222> LOCATION: (7)
<223> OTHER INFORMATION: 2',4'-C-bridged deoxyc ytidine
<220> FEATURE:
<221> NAME/KEY: modified_base
<222> LOCATION: (10)
<223> OTHER INFORMATION: 2',4'-C-bridged deoxyc ytidine
<220> FEATURE:
<221> NAME/KEY: modified_base
<222> LOCATION: (14)
```

```
<223> OTHER INFORMATION: 2',4'-C-bridged deoxycytidine

<400> SEQUENCE: 3
atctctccgc ttcctttc                                              18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial  Sequence:modified_
      base
<220> FEATURE:
<221> NAME/KEY: modified_base
<222> LOCATION: (3)
<223> OTHER INFORMATION: 2',4'-C-bridged deoxycytidine
<220> FEATURE:
<221> NAME/KEY: modified_base
<222> LOCATION: (5)
<223> OTHER INFORMATION: 2',4'-C-bridged deoxycytidine
<220> FEATURE:
<221> NAME/KEY: modified_base
<222> LOCATION: (7)
<223> OTHER INFORMATION: 2',4'-C-bridged deoxycytidine
<220> FEATURE:
<221> NAME/KEY: modified_base
<222> LOCATION: (8)
<223> OTHER INFORMATION: 2',4'-C-bridged deoxycytidine
<220> FEATURE:
<221> NAME/KEY: modified_base
<222> LOCATION: (10)
<223> OTHER INFORMATION: 2',4'-C-bridged deoxycytidine
<220> FEATURE:
<221> NAME/KEY: modified_base
<222> LOCATION: (13)
<223> OTHER INFORMATION: 2',4'-C-bridged deoxycytidine
<220> FEATURE:
<221> NAME/KEY: modified_base
<222> LOCATION: (14)
<223> OTHER INFORMATION: 2',4'-C-bridged deoxycytidine

<400> SEQUENCE: 4
atctctccgc ttcctttc                                              18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial  Sequence:modified_
      base
<220> FEATURE:
<221> NAME/KEY: modified_base
<222> LOCATION: (2)
<223> OTHER INFORMATION: 2',4'-C-bridged thymidine
<220> FEATURE:
<221> NAME/KEY: modified_base
<222> LOCATION: (3)
<223> OTHER INFORMATION: 2',4'-C-bridged deoxycytidine
<220> FEATURE:
<221> NAME/KEY: modified_base
<222> LOCATION: (4)
<223> OTHER INFORMATION: 2',4'-C-bridged thymidine
<220> FEATURE:
<221> NAME/KEY: modified_base
<222> LOCATION: (5)
<223> OTHER INFORMATION: 2',4'-C-bridged deoxycytidine
<220> FEATURE:
<221> NAME/KEY: modified_base
<222> LOCATION: (6)
<223> OTHER INFORMATION: 2',4'-C-bridged thymidine
<220> FEATURE:
<221> NAME/KEY: modified_base
<222> LOCATION: (7)
<223> OTHER INFORMATION: 2',4'-C-bridged deoxycytidine
```

```
<220> FEATURE:
<221> NAME/KEY: modified_base
<222> LOCATION: (8)
<223> OTHER INFORMATION: 2',4'-C-bridged deoxyc ytidine
<220> FEATURE:
<221> NAME/KEY: modified_base
<222> LOCATION: (10)
<223> OTHER INFORMATION: 2',4'-C-bridged deoxyc ytidine
<220> FEATURE:
<221> NAME/KEY: modified_base
<222> LOCATION: (11)
<223> OTHER INFORMATION: 2',4'-C-bridged thymid ine
<220> FEATURE:
<221> NAME/KEY: modified_base
<222> LOCATION: (12)
<223> OTHER INFORMATION: 2',4'-C-bridged thymid ine
<220> FEATURE:
<221> NAME/KEY: modified_base
<222> LOCATION: (13)
<223> OTHER INFORMATION: 2',4'-C-bridged deoxyc ytidine
<220> FEATURE:
<221> NAME/KEY: modified_base
<222> LOCATION: (14)
<223> OTHER INFORMATION: 2',4'-C-bridged deoxyc ytidine
<220> FEATURE:
<221> NAME/KEY: modified_base
<222> LOCATION: (15)
<223> OTHER INFORMATION: 2',4'-C-bridged thymid ine
<220> FEATURE:
<221> NAME/KEY: modified_base
<222> LOCATION: (16)
<223> OTHER INFORMATION: 2',4'-C-bridged thymid ine
<220> FEATURE:
<221> NAME/KEY: modified_base
<222> LOCATION: (17)
<223> OTHER INFORMATION: 2',4'-C-bridged thymid ine

<400> SEQUENCE: 5
atctctccgc ttcctttc                                                    18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial  Sequence:modified_
     base
<220> FEATURE:
<221> NAME/KEY: modified_base
<222> LOCATION: (8)
<223> OTHER INFORMATION: 2',4'-C-bridged thymid ine
<220> FEATURE:
<221> NAME/KEY: modified_base
<222> LOCATION: (13)
<223> OTHER INFORMATION: 2',4'-C-bridged thymid ine

<400> SEQUENCE: 6
cttcctgtct gatggcttc                                                   19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial  Sequence:modified_
     base
<220> FEATURE:
<221> NAME/KEY: modified_base
<222> LOCATION: (6)
<223> OTHER INFORMATION: 2',4'-C-bridged thymid ine
<220> FEATURE:
<221> NAME/KEY: modified_base
<222> LOCATION: (8)
<223> OTHER INFORMATION: 2',4'-C-bridged thymid ine
<220> FEATURE:
```

```
<221> NAME/KEY: modified_base
<222> LOCATION: (10)
<223> OTHER INFORMATION: 2',4'-C-bridged thymid ine
<220> FEATURE:
<221> NAME/KEY: modified_base
<222> LOCATION: (13)
<223> OTHER INFORMATION: 2',4'-C-bridged thymid ine

<400> SEQUENCE: 7
cttcctgtct gatggcttc                                               19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial  Sequence:modified_
      base
<220> FEATURE:
<221> NAME/KEY: modified_base
<222> LOCATION: (2)
<223> OTHER INFORMATION: 2',4'-C-bridged thymid ine
<220> FEATURE:
<221> NAME/KEY: modified_base
<222> LOCATION: (3)
<223> OTHER INFORMATION: 2',4'-C-bridged thymid ine
<220> FEATURE:
<221> NAME/KEY: modified_base
<222> LOCATION: (6)
<223> OTHER INFORMATION: 2',4'-C-bridged thymid ine
<220> FEATURE:
<221> NAME/KEY: modified_base
<222> LOCATION: (8)
<223> OTHER INFORMATION: 2',4'-C-bridged thymid ine
<220> FEATURE:
<221> NAME/KEY: modified_base
<222> LOCATION: (10)
<223> OTHER INFORMATION: 2',4'-C-bridged thymid ine
<220> FEATURE:
<221> NAME/KEY: modified_base
<222> LOCATION: (13)
<223> OTHER INFORMATION: 2',4'-C-bridged thymid ine
<220> FEATURE:
<221> NAME/KEY: modified_base
<222> LOCATION: (17)
<223> OTHER INFORMATION: 2',4'-C-bridged thymid ine
<220> FEATURE:
<221> NAME/KEY: modified_base
<222> LOCATION: (17)
<223> OTHER INFORMATION: 2',4'-C-bridged thymid ine
<220> FEATURE:
<221> NAME/KEY: modified_base
<222> LOCATION: (18)
<223> OTHER INFORMATION: 2',4'-C-bridged thymid ine

<400> SEQUENCE: 8
cttcctgtct gatggcttc                                           19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial  Sequence:modified_base
<220> FEATURE:
<221> NAME/KEY: modified_base
<222> LOCATION: (5)
<223> OTHER INFORMATION: 2',4'-C-bridged deoxyc ytidine
<220> FEATURE:
<221> NAME/KEY: modified_base
<222> LOCATION: (9)
<223> OTHER INFORMATION: 2',4'-C-bridged deoxyc ytidine
<220> FEATURE:
<221> NAME/KEY: modified_base
<222> LOCATION: (16)
```

<223> OTHER INFORMATION: 2',4'-C-bridged deoxyc ytidine

<400> SEQUENCE: 9
cttcctgtct gatggcttc                    19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial   Sequence:modified_
      base
<220> FEATURE:
<221> NAME/KEY: modified_base
<222> LOCATION: (1)
<223> OTHER INFORMATION: 2',4'-C-bridged deoxyc ytidine
<220> FEATURE:
<221> NAME/KEY: modified_base
<222> LOCATION: (2)
<223> OTHER INFORMATION: 2',4'-C-bridged thymid ine
<220> FEATURE:
<221> NAME/KEY: modified_base
<222> LOCATION: (3)
<223> OTHER INFORMATION: 2',4'-C-bridged thymid ine
<220> FEATURE:
<221> NAME/KEY: modified_base
<222> LOCATION: (4)
<223> OTHER INFORMATION: 2',4'-C-bridged deoxyc ytidine
<220> FEATURE:
<221> NAME/KEY: modified_base
<222> LOCATION: (5)
<223> OTHER INFORMATION: 2',4'-C-bridged deoxyc ytidine
<220> FEATURE:
<221> NAME/KEY: modified_base
<222> LOCATION: (6)
<223> OTHER INFORMATION: 2',4'-C-bridged thymid ine
<220> FEATURE:
<221> NAME/KEY: modified_base
<222> LOCATION: (13)
<223> OTHER INFORMATION: 2',4'-C-bridged thymid ine
<220> FEATURE:
<221> NAME/KEY: modified_base
<222> LOCATION: (16)
<223> OTHER INFORMATION: 2',4'-C-bridged deoxyc ytidine
<220> FEATURE:
<221> NAME/KEY: modified_base
<222> LOCATION: (17)
<223> OTHER INFORMATION: 2',4'-C-bridged thymid ine
<220> FEATURE:
<221> NAME/KEY: modified_base
<222> LOCATION: (18)
<223> OTHER INFORMATION: 2',4'-C-bridged thymid ine

<400> SEQUENCE: 10
cttcctgtct gatggcttc                    19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial   Sequence:modified_
      base
<220> FEATURE:
<221> NAME/KEY: modified_base
<222> LOCATION: (1)
<223> OTHER INFORMATION: 2',4'-C-bridged deoxyc ytidine
<220> FEATURE:
<221> NAME/KEY: modified_base
<222> LOCATION: (2)
<223> OTHER INFORMATION: 2',4'-C-bridged thymid ine
<220> FEATURE:
<221> NAME/KEY: modified_base
<222> LOCATION: (3)
<223> OTHER INFORMATION: 2',4'-C-bridged thymid ine

```
<220> FEATURE:
<221> NAME/KEY: modified_base
<222> LOCATION: (4)
<223> OTHER INFORMATION: 2',4'-C-bridged deoxyc ytidine
<220> FEATURE:
<221> NAME/KEY: modified_base
<222> LOCATION: (5)
<223> OTHER INFORMATION: 2',4'-C-bridged deoxyc ytidine
<220> FEATURE:
<221> NAME/KEY: modified_base
<222> LOCATION: (6)
<223> OTHER INFORMATION: 2',4'-C-bridged thymid ine
<220> FEATURE:
<221> NAME/KEY: modified_base
<222> LOCATION: (8)
<223> OTHER INFORMATION: 2',4'-C-bridged thymid ine
<220> FEATURE:
<221> NAME/KEY: modified_base
<222> LOCATION: (9)
<223> OTHER INFORMATION: 2',4'-C-bridged deoxyc ytidine
<220> FEATURE:
<221> NAME/KEY: modified_base
<222> LOCATION: (10)
<223> OTHER INFORMATION: 2',4'-C-bridged thymid ine
<220> FEATURE:
<221> NAME/KEY: modified_base
<222> LOCATION: (13)
<223> OTHER INFORMATION: 2',4'-C-bridged thymid ine
<220> FEATURE:
<221> NAME/KEY: modified_base
<222> LOCATION: (16)
<223> OTHER INFORMATION: 2',4'-C-bridged deoxyc ytidine
<220> FEATURE:
<221> NAME/KEY: modified_base
<222> LOCATION: (17)
<223> OTHER INFORMATION: 2',4'-C-bridged thymid ine
<220> FEATURE:
<221> NAME/KEY: modified_base
<222> LOCATION: (18)
<223> OTHER INFORMATION: 2',4'-C-bridged thymid ine

<400> SEQUENCE: 11
cttcctgtct gatggcttc                                          19
```

NUCLEOSIDES HAVING BICYCLIC SUGAR MOIETY

This application claims priority to and is a continuation of International Application No. PCT/US99/11442, filed May 24, 1999 which claims priority to U.S. Provisional Application No. 60/086719, filed May 28, 1998 and designates the United States.

FIELD OF THE INVENTION

The field of the invention is nucleoside and oligonucleotide analogues and methods for their preparation.

BACKGROUND

Nucleoside and nucleotide analogs have long been used as pharmaceutical ingredients against a variety of viruses and cancers. Currently, a number of nucleoside and nucleotide analogues are in clinical trials for several diseases.

In the cell, nucleosides and nucleotides are phosphorylated or further phosphorylated to the corresponding nucleoside triphosphates. Nucleoside triphosphates serve as inhibitors of DNA or RNA polymerases. Nucleoside triphosphates can also be incorporated into DNA or RNA, which interferes with the elongation of DNA or RNA.

Active nucleoside analogues are generally readily phosphorylated in the target cell. Corresponding nucleoside triphosphates have high affinity to catalytic sites of the polymerases and compete with the natural nucleoside triphosphates as the substrate of the polymerases.

Certain nucleoside analogues work at the nucleoside or the monophosphate level. One group of promising nucleoside analogues is the nucleosides with conformationally locked sugar moieties. It has been reported that certain conformationally locked carbocyclic nucleoside analogues demonstrated potent activity against HCMV, HSV, and EBV (Siddiqui et al. *Nucleosides Nucleotides* 1996, 15, 235–250; Marquez et al. *J. Med. Chem.* 1996, 39, 3739–3747). A conformationally locked, carbocyclic AZT 5'-triphosphate has been reported to be an equipotent inhibitor of HIV reverse transcriptase (Marquez et al. *J. Am. Chem. Soc.* 1998, 120, 2780–2789). Other nucleosides with bicyclic sugar moieties were also prepared even though no activity was found or reported (Chao et al. *Tetrahedron* 1997, 53, 1957–1970; Okabe et al. *Tetrahedron lett.* 1989, 30, 2203–2206, Hong, et al. *Tetrahedron Lett.* 1998, 39, 225–228).

Favorable, conformationally locked nucleosides are expected to have a positive impact on antisense oligonucleotides. Oligonucleotides, as potential antisense therapeutics, have been recognized and explored for two decades. Oligonucleotides are capable of forming double or triple helix with complementary DNA or RNA and have the ability to target the specific sequences in the viral and cancer genome. Specific binding of oligonucleotides to the DNA or RNA targets of interest would inactivate the function associated with the DNA or RNA such as replication, transcription, and translation. Therefore, viral cycles, or cancerous process can be interrupted while the normal cell cycles are not affected.

Since natural oligonucleotides are labile to the cellular and extracellular nucleases, a great deal of efforts has been made on the study of oligonucleotide modifications, especially those modifications aimed at improving nuclease resistance and binding affinity. Oligonucleotides containing certain bicyclic nucleosides have been shown to demonstrate improved nuclease stability (Leumann et al. Bioorg. *Med. Chem. Letts.* 1995, 5, 1231–4; Altmann et al. *Tetrahedron Lett.* 1994, 35, 2331–2334, 7625–7628). Recently, 2'-O,4'-C-methylene ribonucleosides, which have a locked 3'-endo sugar pucker, were synthesized and incorporated into oligonucleotides. Hybridization studies show that conformationally locked nucleosides can significantly enhance hybridization of modified oligonucleotides to the complementary RNA and DNA (Obika et al. *Tetrahedron Lett.* 1997, 38, 8735–8738; Koshkin et al. *Tetrahedron* 1998, 54, 3607–3630).

There is a need for new, conformationally locked nucleosides with bicyclic sugar moieties. These novel nucleosides should be useful in antiviral, anti-cancer, and other therapies. In addition, oligonucleotides composed of these novel, modified nucleosides should have desired stability to cellular nucleases and strong binding affinity to nucleic acid targets. Therefore, these oligonucleotides should be potentially useful in therapeutics and diagnostics.

SUMMARY OF THE INVENTION

Conformationally locked bicyclic-sugar nucleosides, which have a common geometrical shape, and methods for producing conformationally locked bicyclic-sugar nucleosides are described. Nucleosides are provided having bicyclic sugar moieties and oligonucleotides comprising the following formula:

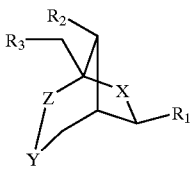

Wherein X, Y and Z are independently selected from a group of O, S, $CH_2$, NR, C=O, C=$CH_2$ or nothing, where R is selected from a group of hydrogen, alkyl, alkenyl, alkynyl, acyl; $R_1$ is selected from a group of adenine, cytosine, guanine, hypoxanthine, uracil, thymine, heterocycles, H, $OCH_3$, OAc, halogen, sulfonate; $R_2$, $R_3$ are independently selected from a group of H, OH, DMTO, TBDMSO, BnO, THPO, AcO, BzO, OP(NiPr$_2$)O(CH$_2$)$_2$CN, OPO$_3$H, PO$_3$H, diphosphate, triphosphate; $R_2$ and $R_3$ together can be PhCHO$_2$, TIPDSO$_2$ or DTBSO$_2$.

The novel nucleosides described herein are anticipated to be useful in antiviral, anti-cancer, and other therapies. Oligonucleotides composed of these modified nucleosides have desired physiological stability and binding affinity that enable them to be useful in therapeutics and diagnostics.

DETAILED DESCRIPTION

Conformationally locked nucleosides which have a 3'-endo sugar pucker, and methods of their preparation are provided. Processes for preparation of previously reported bicyclic nucleoside analogues cannot be applied to the novel nucleoside analogues described herein. The analogues described resulted from the successful linking between C2' and C4' positions of ribose in the nucleoside analogues.

As used herein, the abbreviation "Ac" refers to acetyl; the abbreviation "Bn" refers to benzyl; the abbreviation "Bz" refers to benzoyl; the abbreviation "DMT" refers to dimethoxytrityl; the abbreviation "THP" refers to tetrahydropyranyl; the abbreviation "TBDMS" refers to t-butyldimethylsilyl; the abbreviation "TIPDS" refers to tetraisopropyldisilyl; and the abbreviation "DTBS" refers to di(t-butyl)silyl.

Synthesis of 2,4-Bridged Ribofuranose Derivatives

1-α-Methylarabinose 1, prepared according to a published procedure (Tejima et al. *J. Org. Chem.* 1963, 28. 2999–3003), was protected with 1,1,3,3-tetraisopropyldisiloxanyl (TIPS) at O3 and O5 to give 2, which was converted to the ketone 3 by treatment with DMSO/DCC/TFA. The subsequent Wittig reaction and removal of TIPS afforded the alkene 4 in very good yield. Compound 4 was protected with t-butyidimethylsilyl (TBS) at O5 and with benzyl (Bn) at O3 to give 5. Hydroboration of 5 was conducted with 9-BBN to give exclusively the 2-deoxy-2-hydroxymethyl derivative 6 in excellent yield. 2-deoxy-2-hydroxymethyl derivative 6 was subjected to tritylation with 4,4'-O-dimethoxytrityl (DMT) chloride and removal of TBS with tetrabutylammonium fluoride (TBAF) to yield 7.

Compound 7 was oxidized to give the aldehyde 8, which was treated with formaldehyde and sodium hydroxide to yield the 4-hydroxymethyl derivative 9 in excellent yield. The mesylation of 9 and the subsequent removal of DMT afforded 10. The cyclization effected with NaH in THF and the subsequent removal of the mesyl afforded the bicyclic sugar 11. Treatment of compound 11 with acetic anhydride in the presence of DMAP yields 12, whereas treatment with acetic anhydride/acetic acid in the presence of sulfuric acid

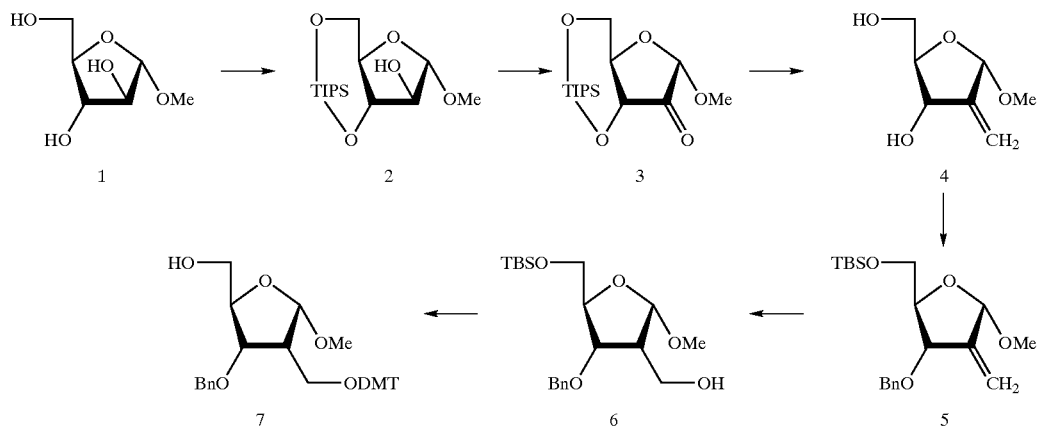

Scheme 1 yields 13, in which the acetoxy at C1 has an inverted orientation (1-β), as compared to the methoxy of 11.

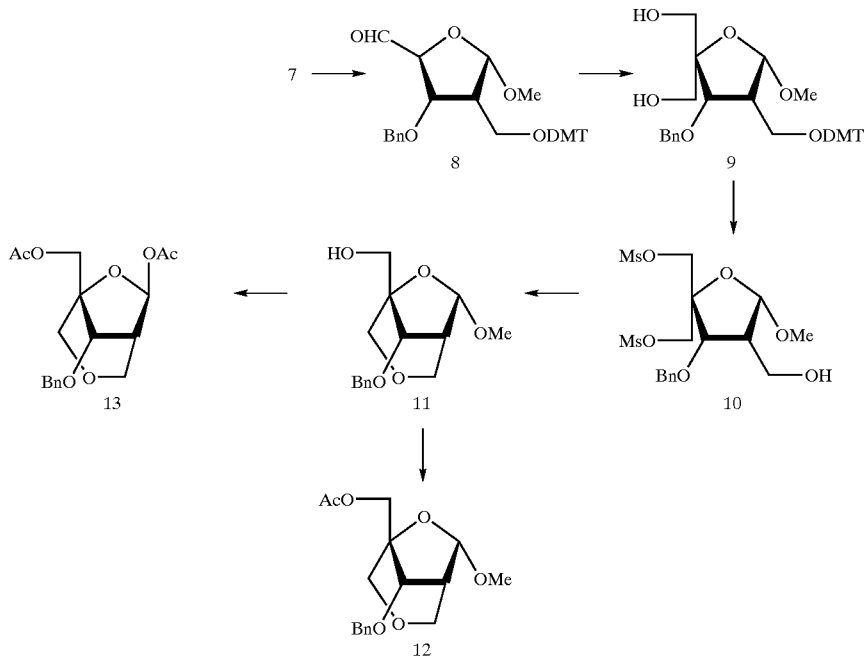

Scheme 2

Synthesis of 2',4'-Bridged Bicyclonucleosides

The bicyclonucleosides having the 2',4'-bridged sugar moiety were synthesized from condensations of silylated nucleoside bases and the bicyclic sugars as shown below. The condensation of 13 with bis(trimethylsilyl)thymine yielded the product 14, the α-anomer, in excellent yield. Treatment of 14 with BCl₃ removed acetyl and benzyl simultaneously to yield the bicyclic α-thymidine 15.

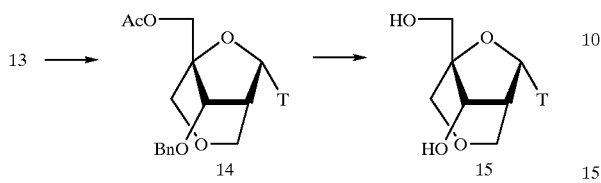

The condensation of 13 with 6-chloro-9-trimethylsilylpurine gave a mixture of the α- and β-purine nucleosides, 16 and 17 (ratio of α: β, 1:1 to 2:3), which could be separated by chromatography.

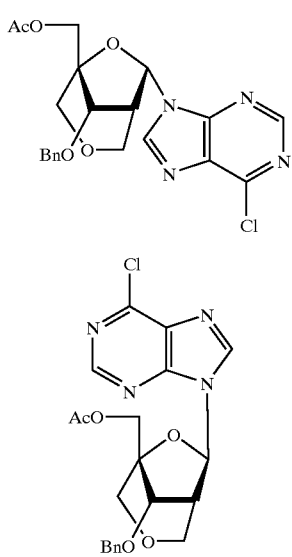

Treatment of 17 and 16 with ammonia in methanol, followed by hydrogenolysis, gave the adenosine analogs 18 and 19, respectively. The hydrogenolysis required a large amount of catalyst material, as well as a prolonged reaction time, because of the increased steric hindrance on the sugar moiety. Treatment of 17 and 16 with mercaptoethanol in the presence of sodium methoxide, followed by hydrogenolysis, yields inosine analogs 20 and 21, respectively.

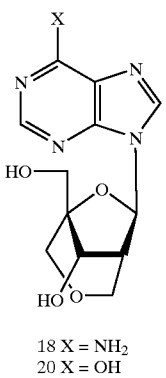

18 X = NH₂
20 X = OH

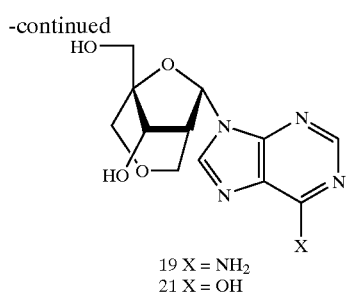

19 X = NH₂
21 X = OH

Condensation of 13 with the silylated $N^2$-acetylguanine yields the α-guanosine derivative 22 as the major product (30%), a small amount of the β-isomer and $N^7$-coupled products. Treatment of the α-guanosine derivative with ammonia in methanol, followed by hydrogenolysis, gave the bicyclic α-guanosine 23.

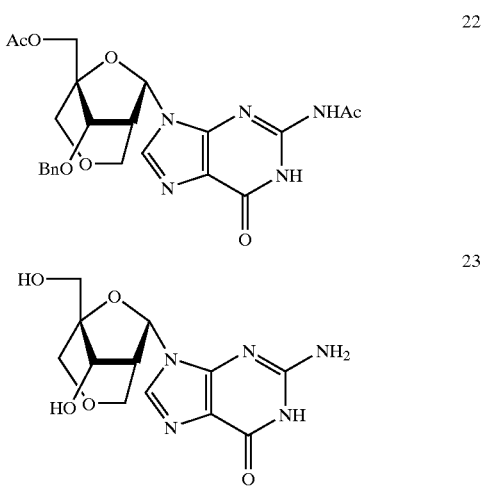

As described above, the condensation reactions yielded either the α-nucleoside, exclusively, or a mixture of the α- and β-nucleosides, without preference for the β-anomers. In order to increase the ratio of β-nucleosides, different condensation conditions were investigated. Temperature had little effect on the ratio of α- and β-anomers. However, the coupling reagent and the functional group at C1 of the sugar did have significant effects on the ratio of α- and β-nucleosides.

Condensation of 12 with bis- or tri(trimethylsilyl) pyrimidines in the presence of tin (IV) chloride gave the β-nucleosides as major products in good yields. Thus, the reaction of 12 with silylated thymine gave the thymidine derivative 24, with β:α ratio of ~4:1. Condensation of 12 with the silylated uracil and $N^4$-benzoylcytosine gave the corresponding nucleosides 25 and 26, respectively, with β:α ratio of ~9:1 in both reactions. Treatment of 24–26 with boron trichloride afforded the pyrimidine bicyclonucleosides 27–29, respectively. In the case of cytidine derivative, the benzoyl group of 29 was removed by treatment with ammonia to give 30. An alternative route (not shown) to prepare 30 started from 28, which was acetylated at O3' and O5', followed by the reaction with triazole and the subsequent treatment with ammonia. In this way, 30 was obtained in moderate yield.

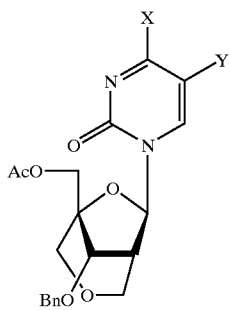

24 X = OH, Y = Me
25 X = OH, Y = H
26 X = NHBz, Y = H

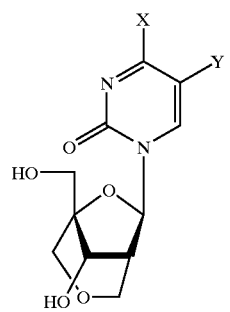

27 X = OH Y = Me
28 X = OH, Y = H
29 X = NHBz, Y = H
30 X = NH$_2$, Y = H

The condensation of 12 with the silylated purines, along with tin (IV) chloride as the coupling reagent, was also investigated. Unlike the reactions with pyrimidines, the condensation of the silylated 6-chloropurine with 12 yielded not only the α- and β-nucleosides 16 and 17, but also an N$^7$-coupling product (not shown). Similarly, the condensation of the silylated N$^2$-acetylguanine with 12 yielded a mixture of three products, the N$^7$-coupled β-nucleosides 31 (42%), the desired β-nucleoside 32 (10%) and the α-nucleoside 22 (6%). However, when heated with the silylated N$^2$-acetylguanine in the presence of trimethylsilyl triflate, the N$^7$-coupled product 31 was partially converted to the N$^9$-coupled, α- and β-bicyclonucleosides 22 (~22%) and 32 (~25%). The separated 32 was subjected to the same treatments as 22 to give the bicyclic β-guanosine 33.

31

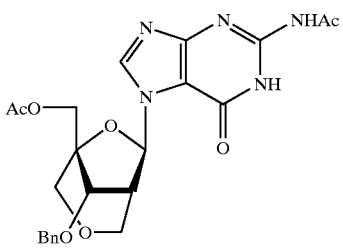

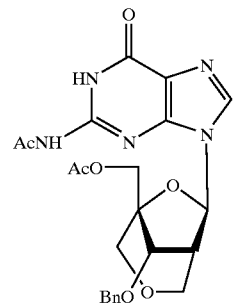

32

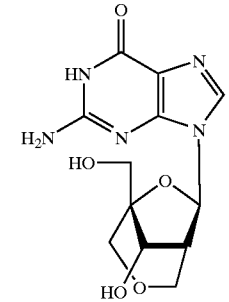

33

Stereochemical assignments of the 2,6-dioxabicyclo[3,2,1]octane derivative 11 and the bicyclonucleosides formed from condensation of bicyclic sugars with silylated nucleoside bases can be assigned by NOE proton NMR. As indicated by a stick-ball model, the rigid dioxabicyclo[3,2,1]octane ring system forces the protons (H1' and H2') at C1' and C2' of the α-bicyclonucleosides to become nearly parallel, whereas the H1' and H2' in the β-bicyclonucleosides direct to the opposite sides. For example, the torsion angle of H1'-C1'-C2'-H2' of the bicyclic α-thymidine 15 after a geometry optimization is 37° and, in consistency with this, a coupling constant of 3.9 Hz in proton NMR was observed. The torsion angle of H1'-C1'-C2'-H2' in the bicyclic β-thymidine 27 is 96° after a geometry optimization and, as expected, no coupling between the H1' and H2' was observed. In fact, the proton at C1' in all the β-bicyclonucleosides measured is a single peak. In contrast, in all the α-bicyclonucleosides measured the proton at C1' is a doublet with a coupling constant of ~4.0 Hz.

The stereochemical assignments of the bicyclonucleosides were further confirmed by X-ray crystal structures of the bicyclic thymidines 15 and 27. The ribose ring of the dioxabicyclo[3,2,1]octane sugar moiety in both compounds adopts a typical C3'-endo sugar pucker while the six-membered ring in the sugar moiety adopts the chair form. The thymine base in both compounds has the anti orientation.

Synthesis of the Phsphoramidites of the 2,4-Bridged Bicyclonucleoside

The bicyclic β-thymidne 27, the bicyclic β-N$^4$-benzoylcytidine 29, and the bicyclic β-N$^4$-acetylcytidine 29 were protected with DMT and then converted to the corresponding phosphoramidites, respectively. Because of the steric hindrance, a longer reaction time was required.

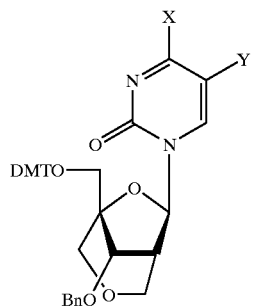

34 X = OH, Y = Me
35 X = NHAc, Y = H
36 X = NHBz, Y = H

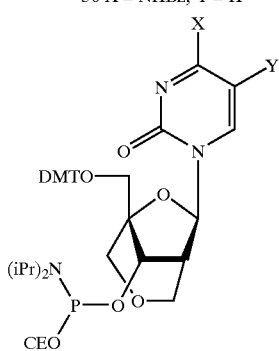

37 X = OH, Y = Me
38 X = NHAc, Y = H
39 X = NHBz, Y = H

EXAMPLES

The synthetic approaches utilized to prepare the compounds described can also be used to synthesize other claimed compounds. The present invention includes, but is not limited to the compounds prepared through the following examples. The numbers in parenthesis following the compound names in the examples correspond to the numbers of the structures in the detailed description section.

Example 1

Preparation of 1-α-Methyl-3,5-O-(1,1,3,3-tetraisopropyl-1,3-disiloxanediyl)-D-ribofuranose (2)

α-Methylarabinose was prepared according to a published procedure (Tejima, S.; Fletcher, Jr. H. G. *J. Org. Chem.* 1963, 28. 2999–3003) and separated from its β-anomer (a minor product) through chromatography on silica. To a stirred solution of α-methylarabinose (19.27 g, 119.9 mmol) in anhydrous pyridine (200 mL) at 0° C. was added 1,3-dichloro-1,1,3,3-tetraisopropyldisiloxane (38.4 mL, 119.9 mmol). The resulting solution was stirred at 0° C. for 1 h and then at room temperature for 1.5 h. The solution was cooled to 0° C. and water (20 mL) added. The mixture was stirred for 10 min and diluted with EtOAc. The aqueous layer was extracted with EtOAc. The combined organic layer was dried ($Na_2SO_4$), and concentrated to dryness. Chromatography on silica with 15% EtOAc in hexanes gave 42.7 g (88%) of the titled compound as a colorless syrup.

Example 2

Preparation of 2-C,2-O-didehydro-α-methyl-3,5-O-(1,1,3,3-tetraisopropyl-1,3-disiloxanediyl)-D-ribofuranose (3)

To a stirred solution of 1-α-methyl-3,5-O-(1,1,3,3-tetraisopropyl-1,3-disiloxane-diyl)-D-ribofuranose (42.6 g, 104.9 mmol) and DCC (43.4 g, 209.8 mmol) in anhydrous DMSO (250 mL) and ether (100 mL) at 0° C. under argon was added a solution of trifluoroacetic acid (4.04 mL, 52.5 mmol) and pyridine (8.44 mL, 105 mmol) in DMSO (30 mL). The resulting reaction mixture was warmed to room temperature, stirred for 5 h, and then cooled to 0° C. Oxalic acid (21.3 g, 236 mmol) in methanol (60 mL) was added, followed by addition of water (30 mL). The resulting mixture was stirred at room temperature for 1 h and the precipitate was filtered and washed thoroughly with hexanes. The filtrate was further diluted with hexanes, washed with water five times, dried ($Na_2SO_4$), and concentrated to dryness. Chromatography on silica with 2% MeOH in methylene chloride-hexanes (1:2) gave 37.6 g (89%) of the titled compound as a colorless syrup; $^1$H NMR ($CDCl_3$) δ 1.00–1.12 (m, 28H, TIPDS), 3.47 (s, 3H, $OCH_3$), 4.05–4.19 (m, 3H, H4, H5a, H5b), 4.51 (dd, J=9.3 Hz, 1.5 Hz, 1H, H3), 4.89 (t, J=1.5 Hz, 1H, H1).

Example 3

Preparation of 2-Deoxy-2-methylene-1-α-methyl-3,5-O-(1,1,3,3-tetraisopropyl-1,3-disiloxanediyl)-D-ribofuranose To a stirred suspension of methyltriphenylphosphonium bromide (21.5 g, 60.1 mmol) in anhydrous ether (1380 mL) at room temperature under argon was added a solution of sodium t-pentoxide (5.97 g, 54.0 mmol) in anhydrous benzene (50 mL). The resulting light-yellow mixture was stirred at room temperature for 6 h and cooled to −10° C., then a solution of 2-C, 2-O-didehydro-α-methyl-3,5-O-(1,1,3,3-tetraisopropyl-1,3-disiloxanediyl)-D-ribofuranose (12.1 g, 30.1 mmol) in ether (35 mL) was added. The reaction mixture was stirred at −10° C. for 1 h, washed with brine twice, dried ($Na_2SO_4$), and concentrated. Chromatography on silica with 5% EtOAc in hexanes gave 11.0 g (91%) of the titled compound as a colorless syrup; $^1$H NMR ($CDCl_3$) δ 1.00–1.12 (m, 28H, TIPDS), 3.45 (s, 3H, $OCH_3$), 3.73 (dt, J=9.0 Hz, 3.0 Hz, 1H, H4), 4.02, 4.03 (2s, 2H, H5), 4.62 (dt, J=9.0 Hz, 2.7 Hz, 1H, H3), 5.27 (m, 1H, H1), 5.32–5.36 (m, 2H, H2').

Example 4

Preparation of 2-Deoxy-2-methylene-1-α-methyl-D-ribofuranose (4)

To a stirred solution of 2-deoxy-2-methylene-1-α-methyl-3,5-O-(1,1,3,3-tetraiso-propyl-1,3-disiloxanediyl)-D-ribofuranose (35.0 g, 87.1 mmol) in THF (200 mL) was added 1.0 M TBAF in THF (180 mL). The resulting solution stood at room temperature for 1 h. THF was evaporated and the residue chromatographed on silica with 10% EtOH in methylene chloride to give 14.6 g (88%) of the titled compound as a syrup.

Example 5

Preparation of 3-O-benzyl-5-O-(t-butyidimethylsilyl)-2-deoxy-2-methylene-1-α-methyl-D-ribofuranose (5)

A solution of 2-deoxy-2-methylene-1-α-methyl-D-ribofuranose (13.7 g, 85.5 mmol) and TBDMS-Cl (13.5 g, 89.6 mmol) in anhydrous pyridine (130 mL) stood at room temperature for 15 h. After cooling to 0° C. and addition of water (2 mL), the resulting mixture was stirred at room temperature for 1 h, concentrated to half the volume, diluted with EtOAc, washed with brine, dried (Na$_2$SO$_4$), and concentrated to dryness. The thoroughly dried crude was dissolved in THF (70 mL) and added to a stirred mixture of NaH (60% in mineral oil, 5.6 g, 140 mmol) in THF (350 mL) at 0° C. After stirring at room temperature for 40 min, benzyl bromide (10.75 mL, 90.5 mmol) was added. The reaction mixture was stirred for 4 h and cooled to 0° C., followed by slow addition of water (2 mL) and then 10% AcOH in water until pH 7. The mixture was diluted with EtOAc, washed with brine, then with dilute sodium bicarbonate, dried (Na$_2$SO$_4$), and concentrated to dryness. Chromatography on silica with 0–10% EtOAc in hexanes gave 23.8 g (76%) of the titled compound as a colorless liquid; $^1$H NMR (CDCl$_3$) δ 0.01 (s, 3H, SiCH$_3$), 0.02 (s, 3H, SiCH$_3$), 0.85 (s, 9H, t-Bu), 3.41 (s, 3H, OCH$_3$), 3.60–3.72 (m, 2H, H5a, H5b), 4.20 (dd, J=8.7 Hz, 4.5 Hz, 1H, H3), 4.57, 4.66 (AB, J=12.0 Hz, 2H, Bn), 5.22 (t, J=1.2 Hz, 1H, H1), 5.38 (t, J=1.5 Hz, 1H, H2a'), 5.43 (m, J=1.2 Hz, 1H, H2b'), 7.23–7.37 (m, 5H, Bn); Anal. Calcd. for C$_{20}$H$_{32}$O$_4$Si: C, 65.89; H, 8.85. Found: C, 65.92; H, 9.22.

Example 6

Preparation of 3-O-Benzyl-5-O-(t-butyldimethylsilyl)-2-deoxy-2-hydroxymethyl-1-α-methyl-D-ribofuranose (6)

To a stirred solution of 3-O-benzyl-5-O-(t-butyldimethylsilyl)-2-deoxy-2-methylene-1-α-methyl-D-ribofuranose (5.28 g, 14.50 mmol) under argon was added 9-BBN (0.5 M in THF, 87 mL). The resulting solution was stirred at ambient temperature for 1 h, then at 40° C. overnight, cooled to room temperature, and transferred to a flask containing sodium perborate tetrahydrate (13.39 g, 87 mmol) in water (85 mL) and ethanol (85 mL). The resulting mixture was vigorously stirred at 50° C. for 4 h, cooled to 0° C., neutralized with AcOH to pH 8, and concentrated to a small volume. The remaining volume was diluted with water (20 mL) and extracted with methylene chloride three times. The combined organic layer was washed with brine twice, dried (Na$_2$SO$_4$), and concentrated to dryness. Chromatography on silica with EtOAc-hexanes (1:2) gave 5.17 g (93%) of the titled compound as a colorless syrup; $^1$H NMR (CDCl$_3$) δ 0.03 (s, 6H, SiCH$_3$), 0.87 (s, 9H, t-butyl), 2.34–2.43 (m, 1H, H2), 3.39 (s, 3H, OCH3), 3.48 (dd, J=10.5 Hz, 6.0 Hz, 1H, H5a), 3.60 (dd, J=10.5 Hz, 3.6 Hz, 1H, H5b), 3.88 (d, J=7.2 Hz, 2H, H2'), 3.98 (dd, J=7.2 Hz, 2.7 Hz, 1H, H3), 4.17 (m, 1H, H4), 4.44, 4.66 (AB, J=12.3 Hz, 2H, Bn), 4.95 (d, J=5.4 Hz, 1H, H1), 7.23–7.36 (m, 5H, Bn); Anal. Calcd. for C$_{20}$H$_{34}$O$_5$Si: C, 62.79; H, 8.96. Found: C, 62.92; H, 9.21.

Example 7

Preparation of 3-O-benzyl-2-deoxy-2-(4,4'-dimethoxytrityloxymethyl)-1-α-methyl-D-ribofuranose (7)

A solution of 3-O-benzyl-5-O-(t-butyldimethylsilyl)-2-deoxy-2-hydroxymethyl-1-α-methyl-D-ribofuranose (6.60 g, 17.28 mmol) and DMT-Cl (7.03 g, 20.74 mmol) in anhydrous pyridine (50 mL) stood at room temperature overnight and the reaction was quenched by adding water (8 mL). The resulting solution stood for 10 min and was diluted with EtOAc, washed with brine three times, dried (Na$_2$SO$_4$), and concentrated to give the crude 9, which was dissolved in THF (52 mL). TBAF (1.0 M in THF, 26 mL) was added and the resulting solution stood at room temperature for 30 min. THF was evaporated and the residue chromatographed on silica with EtOAc-hexane (1:1) to give 9.28 g (94%) of the titled compound as a white foam; $^1$H NMR (CDCl$_3$) δ 2.33–2.42 (m, 1H, H2), 3.26–3.63 (m, 7H, H5a, H5b, H2a', H2b', OCH$_3$), 3.79 (d, J=1.2 Hz, 6H, DMT), 3.91 (dd, J=7.5 Hz, 2.4 Hz, 1H, H3), 4.13 (m, 1H, H4), 4.41, 4.50 (AB=12.9 Hz, 2H, Bn), 5.05 (d, J=5.1 Hz, 1H, H1), 6.78–6.85 (m, 4H, DMT), 7.14–7.47 (m, 14H, Bn, DMT); Anal. Calcd. for C$_{35}$H$_{38}$O$_7$: C, 73.66; H, 6.71. Found: C, 73.57; H, 6.76.

Example 8

Preparation of 3-O-benzyl-2-deoxy-2-(4,4'-dimethoxytrityloxymethyl)-5-C,5-O-didehydro-1-α-methyl-D-ribofuranose (8)

To a stirred solution of 3-O-benzyl-2-deoxy-2-(4,4'-dimethoxytrityloxymethyl)-1-α-methyl-D-ribofuranose (9.18 g, 16.16 mmol) and DCC (10.0 g, 48.49 mmol) in anhydrous DMSO (60 mL) at 10° C. was added a solution of trifluoroacetic acid (0.622 mL, 8.08 mmol) and pyridine (1.95 mL, 24.24 mmol) in DMSO (5l mL). The resulting reaction mixture was stirred at 10° C. for 1 h, at room temperature for 6 h, and then cooled to 0° C. After addition of water (8 mL), the mixture was stirred overnight and diluted with EtOAC. The precipitate was filtered and thoroughly washed with EtOAc. The combined filtrate was washed with brine five times, dried (Na$_2$SO$_4$), and concentrated to dryness. Chromatography on silica with EtOAc-hexanes (1:1) gave 8.26 g (90%) of the titled compound as a white foam.

Example 9

Preparation of 3-O-benzyl-2-deoxy-2-(4,4'-dimethoxytrityloxymethyl)-4-C-hydroxymethyl-1-α-methyl-D-ribofuranose (9)

To a stirred solution of 3-O-benzyl-2-deoxy-2-(4,4'-dimethoxytrityloxymethyl)-5-C,5-O-didehydro-1-α-methyl-D-ribofu-ranose (8.0 g. 14.08 mmol) and formaldehyde (37% in water, 85 mL) in dioxane (420 mL) at 0° C. was added dropwise an aqueous NaOH solution (2.0 M, 210 mL) during 15 min. The resulting cloudy solution was stirred at room temperature for 2 days to become a clear solution. After cooling to 0° C., the solution was neutralized with 10% acetic acid to pH 8, concentrated to a small volume, diluted with water (100 mL), and extracted with methylene chloride three times. The combined organic layer was washed with brine, dried (Na$_2$SO$_4$), and concentrated to dryness. Chromatography on silica with 4–5% ethanol in methylene chloride gave 8.11 g (94%) of the titled compound as a white foam; $^1$H NMR (CDCl$_3$) δ 2.46–2.57 (m, 1H, H2), 3.23–3.73 (m, 9H, H5, H4', H2', OCH$_3$), 3.79 (d, J=1.8 Hz, 6H, DMT), 4.14 (d, J=6.9 Hz, 1H, H3), 4.43, 4.47 (AB, J=12 Hz, 2H, Bn), 4.97 (d, J=4.8 Hz, 1H, H1), 6.77–6.85 (m, 4H, DMT), 7.11–7.46 (m, 14H, Bn, DMT).

Example 10

Preparation of 3-O-benzyl-2-deoxy-2-hydroxymethyl-5-O-mesyl-4-mesyloxymethyl-1-α-methyl-D-ribofuranose (10)

To a stirred solution of 3-O-benzyl-2-deoxy-2-(4,4'-dimethoxytrityloxymethyl)-4-C-hydroxymethyl-1-α-methyl-D-ribofu-ranose (7.80 g, 13.0 mmol) in anhydrous pyridine (60 mL) at 0° C. under argon was added dropwise methanesulfonyl chloride (3.03 mL, 39 mmol). The resulting reaction mixture was stirred at room temperature for 45 min, cooled to 0° C., and diluted by adding water (5 mL). The resulting mixture was stirred at room temperature for 15 min, diluted with EtOAc, washed with brine three times, dried ($Na_2SO_4$), and concentrated to give the crude as a white foam, which was dissolved in AcOH-Water (80:20, 400 mL). The resulting solution stood at room temperature for 2 h and was diluted with water (200 mL), and concentrated to about a quarter of the volume. Water (100 mL) was added and the mixture concentrated to dryness. Chromatography on silica with EtOAc-hexanes (3:1 to 1:0) gave 5.32 g (90%) of the titled compound as a semi-solid; $^1$H NMR ($CDCl_3$) δ 2.43–2.54 (m, 1H, H2), 3.01 (s, 3H, OMs), 3.03 (s, 3H, OMs), 3.41 (s, 3H, $OCH_3$), 3.81 (d, J=4.8 Hz, 2H, H2'), 4.01 4.04 (AB, J=10.5 Hz, 2H, H4'), 4.21 (d, J=7.5 Hz, 1H, H3), 4.30,4.50 (AB, J=1.8 Hz, 2H, H5), 4.56, 4.63 (AB, J=12.0 Hz, 2H, Bn), 4.99 (d, J=5.1 Hz, 1H, H1), 7.30–7.42 (m, 5H, Bn); Anal. Calcd. for $C_{17}H_{27}O_{10}S_2$: C, 44.82; H, 5.97. Found: C, 44.68; H, 6.00.

Example 11

Preparation of (1S,3S,4R,8S)-8-benzyloxy-1-hydroxymethyl-3-methoxy-2,6-dioxabicyclo[3,2,1]octane (11)

To a stirred mixture of NaH (60% in mineral oil, 1.83 g, 22.90 mmol) in anhydrous THF (200 mL) was added a solution of 3-O-benzyl-2-deoxy-2-hydroxymethyl-5-O-mesyl-4-mesyloxymethyl-1-α-methyl-D-ribofuranose (5.20 g, 11.45 mmol) in THF (30 mL). The resulting reaction mixture was stirred at 55° C. for 42 h and the reaction quenched by adding water at 0° C. THF was evaporated and an aqueous NaOH (0.5 M, 250 mL) added. The resulting mixture was heated at reflux for 24 h, cooled to 0° C., neutralized with dilute hydrochloric acid to pH 8, extracted with methylene chloride four times. The combined organic layer was dried ($Na_2SO_4$) and concentrated to dryness. Chromatography on silica with EtOAc-hexanes (2:1 to 1:0) gave 3.16 g (98%) of the titled compound as a colorless syrup; $^1$H NMR ($CDCl_3$) δ 2.32 (m, 1H, H2), 3.41 (d, J=11.4 Hz, 1H, H4a'), 3.46–3.60 (m, 2H, 5H, H5, $OCH_3$), 3.91 (d, J=11.1 Hz, 1H, H4b'), 3.92 (dd, J=10.8 Hz, 2.4 Hz, 1H, H2a'), 4.01 (d, J=5.4 Hz, 1H, H3), 4.04 (d, J=10.5 Hz, 1H, H2b'), 4.58, 4.64 (AB, J=12.0 Hz, Bn), 5.07 (d, J=3.9 Hz, 1H, H1), 7.28–7.40 (m, 5H, Bn).

Example 12

Preparation of (1R,3S,4R,8S)-1-acetoxymethyl-8-benzyloxy-3-methoxy-2,6-dioxabicyclo[3,2,1]octane (12)

A solution of (1S,3S,4R,8S)-8-benzyloxy-1-hydroxymethyl-3-methoxy-2,6-dioxabicyclo[3,2,1]octane (1.60 g, 5.71 mmol), acetic anhydride (1.08 mL, 11.42 mmol), and DMAP (2.09 g, 17.13 mmol) in anhydrous methylene chloride (10 mL) was stirred at room temperature for 2 h, cooled to 0° C., and diluted with methanol (4 mL). The mixture was stirred at room temperature for 15 min, diluted with methylene chloride, washed with brine and then with 10% $NaHCO_3$, dried ($Na_2SO_4$), and concentrated to dryness. Chromatography on silica with ethyl acetate-hexanes (1:1) gave 1.82 g (99%) of the titled compound as a colorless syrup; $^1$H NMR ($CDCl_3$) δ 2.02 (s, 3H, OAc), 2.33 (m, 1H, H2), 3.50 (d, J=10.8 Hz, 1H, H4a'), 3.57 (s, 3H, $OCH_3$), 3.86–4.04 (m, 5H, H2a', H2b', H3, 114b', H5a), 4.14 (d, J=12.0 Hz, 1H, H5b), 4.50, 4.64 (AB, J=12.0 Hz, 1H, Bn), 5.09 (d, J=3.9 Hz,1H, H1), 7.29–7.42 (m, 5H, Bn); Anal. Calcd. for $C_{17}H_{22}O_6$: C, 63.34; H, 6.88. Found: C. 63.41; H, 6.94.

Example 13

Preparation of (1R,3S,4R,8S)-3-acetoxy-1-acetoxymethyl-8-benzyloxy-2,6-dioxabicyclo[3,2,1]octane (13)

To a stirred solution of (1S,3S,4R,8S)-8-benzyloxy-1-hydroxymethyl-3-methoxy-2,6-dioxabicyclo[3,2,1]octane (600 mg, 2.14 mmol) in a mixture of acetic acid (6.0 mL) and acetic anhydride (0.6 mL) at 0° C. was added dropwise concentrated sulfuric acid (57 µL, 1.07 mmol). The resulting reaction mixture was stirred at 0° C. for 10 min and then at room temperature for 2 h. After cooling to 0° C., the solution was diluted with EtOAc, washed with brine three times and then with 10% sodium bicarbonate, dried ($Na_2SO_4$), and concentrated to dryness. Chromatography on silica with EtOAc-hexanes (2:3) gave 696 mg (93%) of the titled compound (β-anomer) and 31 mg (3%) of the β-anomer, both as a colorless syrup. The β-anomer was solidified after standing at room temperature for days; m.p. 55–58° C.; $^1$H NMR ($CDCl_3$) δ 2.03 (s, 3H, OAc), 2.08 (s, 3H, OAc), 2.36–2.39 (m, 1H, H2), 3.49 (d, J=10.8 Hz, H4a'), 3.73 (d, J=11.1 Hz, 2.7 Hz, 1H, H2a'), 3.89 (d, J=11.1 Hz, 1H, H4b'), 4.01 (d, J=11.1 Hz, 1H, H2b'), 4.03 (d, J=9.3 Hz, 1H, H5a), 4.14 (d, J=5.1 Hz, 1H, H3), 4.55 (d, J=9.6 Hz, 1H, H5), 4.55, 4.64 (AB, J=11.7 Hz, 2H, Bn), 6.39 (s, 1H, H1), 7.29–7.42 (m, 5H, Bn); Anal. Calcd. for $C_{18}H_{22}O_7$: C, 61.70; H, 6.33. Found: C, 61.74; H, 6.46.

Example 14

Preparation of (1R,3S,4R,8S)-1-acetoxymethyl-8-benzyloxy-3-(thymin-1-yl)-2,6-dioxabicyclo[3,2,1]octane (14)

A mixture of thymine (189 mg, 1.5 mmol) and anhydrous ammonium sulfate (15 mg) in HMDS (6 mL) was heated at reflux overnight. After removal of HMDS, the residue was co-evaporated with anhydrous m-xylene, dried under vacuum for 30 min, and dissolved in a solution of (1R, 3S,4R,8S)-3-acetoxy-1-acetoxymethyl-8-benzyloxy-2,6-dioxabicyclo[3,2,1]octane (306 mg, 0.87 mmol) in 1,2-dichloroethane (5 mL). To this stirred solution under argon was added dropwise trimethylsilyl triflate (0.38 mL) in 1,2-dichloroethane (2 mL). The resulting solution was heated under reflux for 2 h, cooled to 0° C., diluted with chloroform, and neutralized with 10% $NaHCO_3$ (10 mL). The organic layer was separated and the aqueous layer extracted with chloroform twice. The combined organic layer was dried ($Na_2SO_4$) and concentrated to dryness. Crystallization from EtOAc-$CH_2Cl_2$ gave the titled compound (303 mg, 83%) as a colorless solid; m.p. 198–200° C.; $^1$H NMR ($CDCl_3$) δ 1.94 (d, J=1.2 Hz, 1H, $ArCH_3$), 2.04 (s, 3H, OAc), 2.93 (m, 1H, H2'), 3.50 (dd, J=11.8 Hz, 2.1 Hz, 1H, H2a"), 3.59 (d, J=11.4 Hz, 1H, H4a"), 4.016 (d, J=11.7 Hz, 1H, H4b"), 4.022 (d, J=12.6 Hz, 1H, H5a'), 4.09 (d, J=12.0 Hz, 1H, H2b"), 4.11 (d, J=4.5 Hz, 1H, H3'), 4.27 (d, J=12.6 Hz, 1H, H5b'), 4.53, 4.70 (AB, J=11.7 Hz, 2H, Bn), 5.88 (d, J=3.6 Hz,1H, H1'), 7.30–7.42 (m, 5H, Bn), 7.74 (d, J=1.5 Hz, 1H, H6), 8.79 (s, 1H, NH); Anal. Calcd. for $C_{21}H_{24}N_2O_7$: C, 60.57: H, 5.81; N, 6.73. Found: C, 60.55; H, 5.84; N. 6.69.

Example 15

Preparation of (1S,3S,4R,8S)-8-hydroxy-1-hydroxymethyl-3-(thymin-1-yl)-2,6-dioxabicyclo[3,2,1]octane (15)

To a solution of (1R,3S,4R,8S)-1-acetoxymethyl-8-benzyloxy-3-(thymin-1-yl)-2,6-dioxabicyclo[3,2,1]octane in anhydrous methylene chloride (3 mL) at 10° C. was added boron trichloride (1.0 M in $CH_2Cl_2$, 6 mL). The resulting reaction mixture was stirred at 15° C. to room temperature overnight and cooled to 0° C. Methanol (1.5 mL) was added dropwise and the resulting mixture stirred at 0° C. for 15 min, followed by addition of triethylamine (2 mL). The solvent was evaporated and the precipitate thoroughly extracted with warm acetone. The acetone solution was dried ($Na_2SO_4$) and concentrated to dryness. Chromatography on silica with 10% methanol in chloroform gave 99 mg of 20 as a white foam. Crystallization from acetone gave 95 mg (93%) of the titled compound as a colorless solid; m.p. 225–226° C.; $^1H$ NMR (DMSO-$d_6$) δ 1.76 (d, J=0.9 Hz, 1H, $ArCH_3$), 2.45 (m, 1H, H2'), 3.25 (dd, J=11.4 Hz, 2.1 Hz, 1H, H2a"), 3.32–3.52 (m, 2H, H5'), 3.53 (d, J=11.4 Hz, 1H, H4a"), 3.72 (d, J=11.1 Hz, 1H, H4b"), 3.93 (d, J=11.1 Hz, 1H, H2b"), 4.16 (m, 1H, H3'), 4.84 (t, J=6.0 Hz, 1H, OH), 5.74 (d, J=4.2 Hz,1H, H1'), 5.84 (d, J=3.9 Hz, 1H, OH), 7.76 (d, J=1.2 Hz, 1H, H6), 11.32 (s, 1H, NH); MS m/z 285 ($MH^+$); Anal. Calcd. for $C_{12}H_{16}N_2O_6$: C, 50.70; H, 5.67; N, 9.85. Found: C, 50.85; H, 5 5.68; N, 9.75.

Example 16

Preparation of (1R,3R,4R,8S)-1-acetoxymethyl-8-benzyloxy-3-(6-chloropurin-9-yl)-2,6-dioxabicyclo[3,2,1]octane (17) and (1R,3S,4R,8S)-1-acetoxymethyl-8-benzyloxy-3-(6-chloropurin-9-yl)-2,6-dioxabicyclo[3,2,1]-octane (16)

A mixture of 6-chloropurine (246 mg, 1.6 mmol) and HMDS (8.0 mL) was refluxed under argon for 2 h. HMDS was evaporated and the residue dried under vacuum for 30 min and then dissolved in a solution of (1R,3S,4R,8S)-3-acetoxy-1-acetoxymethyl-8-benzyloxy-2,6-dioxabicyclo[3,2,1]octane (302 mg, 0.83 mmol) in anhydrous 1,2-dichloroethane (5.0 mL), followed by addition of trimethylsilyl triflate (0.38 mL, 2.25 mmol) in 1,2-dichloroethane (2.0 mL). The resulting solution was heated at reflux under argon for 45 min. The work up was the same as that described before. Chromatography on silica with EtOAc-hexanes (1:1) gave (1R,3S,4R,8S)-1-acetoxymethyl-8-benzyloxy-3-(6-chloropurin-9-yl)-2,6-dioxabicyclo[3,2,1]-octane (122 mg, α-anomer) and (1R, 3R, 4R, 8S)-1-acetoxymethyl-8-benzyloxy-3-(6-chloropurin-9-yl)-2,6-dioxabicyclo-[3,2,1]octane (157 mg, β-anomer), both as a colorless solid. Total yield was 75%. The α-isomer: $^1H$ NMR (CDCl$_3$) δ 2.05 (s, 3H, OAc), 2.89 (m, 1H, H2'), 3.23 (dd, J=12.0 Hz, 2.4 Hz, 1H, H2a"), 3.72 (d, J=11.7 Hz, H4a"), 4.09 (d, J=12.3 Hz, 2H, H4", H5a'), 4.13 (d, J=13.2 Hz, 1H, H2b"), 4.24 (d, J=4.8 Hz, H3'), 4.29 (d, J=12.3 Hz, 1H, H5b'), 4.60, 4.74 (AB, J=11.7Hz, 2H, Bn), 6.50 (d, J=4.2 Hz, 1H, H1'), 7.32–7.44 (m, 5H, Bn), 8.69 (s, 1H, H8), 8.78 (s, 1H, H2). The βisomer: m.p. 124–125° C. (EtOAc-hexanes); $^1H$ NMR (CDCl$_3$) δ 2.05 (s, 3H, OAc), 2.90 (m, 1H, H2'), 3.55 (d, J=11.1 Hz, H4a"), 3.95–4.03 (m, 2H, H2a", H4b"), 4.18–4.24 (m, 3H, H5', H2b"), 4.32 (d, J=4.8 Hz, H3'), 4.47, 4.63 (AB, J=11.7 Hz, 2H, Bn), 6.52 (s, 1H, H1'), 7.24–7.35 (m, 5H, Bn), 8.40 (s, 1H, H8), 8.72 (s, 1H, H2); Anal. Calcd. for $C_{21}H_{21}N_4O_5Cl$: C, 56.70; H, 4.76; N, 12.59. Found: C, 56.36; H, 4.56; N, 12.37.

Example 17

Preparation of (1R,3S,4R,8S)-1-acetoxymethyl-3-($N^2$-acetylguanin-9-yl)-8-benzyloxy-2,6-dioxabicyclo[3,2,1]octane (22)

A mixture of $N^2$-acetyl guanine (193 mg 1.0 mmol) and ammonium sulfate (20 mg) in pyridine (1.0 mL) and HMDS (5.0 mL) was refluxed under argon for 3 h. The resulting clear solution was concentrated and co-evaporated with xylene (10 mL, sodium dried). The residue was dried under vacuum at 50° C. for 1 h and dissolved in a solution of (1R,3S,4R,8S)-3-acetoxy-1-acetoxymethyl-8-benzyloxy-2,6-dioxabicyclo[3,2,1]octane (175 mg, 0.5 mmol) in anhydrous 1,2-dichloroethane (5.0 mL), followed by addition of trimethylsilyl triflate (0.27 mL, 1.5 mmol) in 1,2-dichloroethane (1.0 mL). The resulting solution was stirred at room temperature under argon for 30 min, then heated at 70–75° C. for 2 h, cooled to 0° C., and neutralized with 10% sodium bicarbonate (10 mL). The resulting mixture was stirred for 15 min and the organic layer separated. The aqueous layer was extracted with chloroform twice. The combined organic layer was dried ($Na_2SO_4$) and concentrated to dryness. Chromatography on silica with 10% ethanol in $CHCl_3$-EtOAc (1:1) gave the titled compound (72 mg, 30%) as a colorless solid; m.p. 249° C. (decom., EtOAc); $^1H$ NMR (CDCl$_3$) δ 2.01 (s, 3H, OAc), 2.29 (s, 3H, NAc), 2.75 (m, 1H, H2'), 3.29 (dd, J=11.7 Hz, 1.8 Hz, 1H, H2a"), 3.66 (d, J=11.4 Hz, 1H, H4a"), 4.03 (d, J=11.4 Hz, 1H, H4b"), 4.05 (d, J=11.7 Hz, 1H, H2b"), 4.70 (d, J=12.3 Hz, 1H, H5a'), 4.13 (d, J=4.8 Hz, H3'), 4.23 (d, J=12.3 Hz, 1H, H5b'), 4.53. 4.67 (AB, J=11.7 Hz, 2H, Bn), 6.17 (d, J=4.2 Hz, 1H, H1'), 7.28–7.40 (m, 5H, Bn), 8.32 (s, 1H, H8), 9.80 (s, 1H, NH), 12.12 (s, 1H, NH).

Example 18

Preparation of (1S,3R,4R,8S)-3-(adenin-9-yl)-8-hydroxy-1-hydroxymethyl-2,6-dioxabiciclo[3,2,1]octane (18)

A solution of (1R,3R,4R,8S)-1-acetoxymethyl-8-benzyloxy-3-(6-chloropurin-9-yl)-2,6-dioxabicyclo[3,2,1]-octane (100 mg, 0.225 mmol) in a mixture of dioxane (20 mL) and 30% aqueous ammonium hydroxide (20 mL) was heated in a steel bomb at 100° C. for 16 h. Solvents were evaporated and the residue was dissolved in methanol, followed by addition of 20% palladium hydroxide on charcoal (~50% water, 3×250 mg, added each day). The hydrogenolysis was conducted at room temperature under 55 psi hydrogen for 4 days. The catalyst was filtered and washed with methanol. The combined methanol solution was concentrated and the residue chromatographed on silica with 20% methanol in methylene chloride to give the titled compound (39 mg, 59%) as a colorless solid, which was crystallized from methanol; m.p. 250° C. (decom.); $^1H$ NMR (DMSO-$d_6$+$D_2O$): δ 2.53 (m, 1H, H2'), 3.33 (d, J=11.1 Hz, 1H, 1H2a"), 3.40 (d, J=12.3 Hz, 1H, H5a'), 3.50 (d, J=12.6 Hz, 1H, H5b'), 3.69–3.76 (m, 2H, H2b", H4a"), 4.05 (d, J=10.2 Hz, H4b"), 4.45 (d, J=5.1 Hz, 1H, H3), 6.26 (s, 1H, H1'), H1'), 7.28 (m, 2H, $NH_2$), 8.12 (s, 1H, H8), 8.33 (s, 1H, H2); MS: 294 ($MH^+$); Anal. Calcd. for $C_{12}H_{15}N_5O_4$: C, 49.14; H, 5.16; N, 23.88. Found: C, 49.01; H, 4.97; N, 23.92.

Example 19

Preparation of (1S,3S,4R,8S)-3-(adenin-9-yl)-8-hydroxy-1-hydroxymethyl-2,6-dioxabicyclo[3,2,1]octane (19)

A similar procedure as described in Example 18 gave the titled compound (43 mg, 65%) as a colorless solid from (1R,3S,4R,8S)-1-acetoxymethyl-8-benzyloxy-3-(6-chloropurin-9-yl)-2,6dioxabicyclo[3,2,1]octane (100 mg). $^1H$ NMR (CD$_3$OD): δ 2.71 (m, 1H, H2'), 3.13 (dd, J=11.7 Hz, 2.4 Hz, 1H, H2a"), 3.57 (d, J=12.6 Hz., 1H, H5a'), 3.64 (d, J=11.1 Hz, 1H, H4a"), 3.68 (d, J=12.3 Hz, 1H, H5b'), 3.96 (d, J=11.1 Hz, 1H, H4b"), 4.14 (d, J=11.7 Hz, 1H, H2b"), 6.39 (d, J$^{32}$ 4.2 Hz, 1H, H1'), 8.04 (s, 1H, H8), 8.44 (s, 1H, H2); MS m/z 294 (MH$^+$).

Example 20

Preparation of (1S,3R,4R,8S)-8-hydroxy-1-hydroxymethyl-3-(hypoxanthin-9-yl)-2,6-dioxabicyclo[3,2,1]octane (20)

To a solution of (1R,3R,4R,8S)-1-acetoxymethyl-8-benzyloxy-3-(6-chloropurin-9-yl)-2,6-dioxabicyclo[3,2,1]-octane (150 mg, 0.34 mmol) and muercaptoethanol (0.19 mL, 2.7 mmol) in methanol (20 mL) was added sodium methoxide (0.37 mL of 5.4 M in methanol, 2.0 mmol). The resulting solution was heated under reflux for 6 h, cooled to room temperature, neutralized with 10% AcOH to pH 7. Methanol was evaporated and the residue diluted with 1.0 M NaHCO$_3$ (15 mL), followed by extraction with 10% methanol in chloroform until the aqueous phase did not contain the product. The combined organic layer was dried (Na$_2$SO$_4$) and concentrated to dryness. Chromatography on silica with 10–1 5% methanol in chloroform gave 109 mg (84%) of the inosine derivative (not shown) as a colorless solid, 100 mg (0.26 mmol) of which was dissolved in methanol, followed by addition of 20% palladium hydroxide on charcoal (50% water, 600 mg). The hydrogenolysis was conducted at room temperature under 50 psi hydrogen for 3 days. The catalyst was filtered and washed with methanol. The combined methanol solution was concentrated and the residue chromatographed on silica with 20–25% methanol in methylene chloride to give 61 mg (61%) of the titled compound as a colorless solid, which was crystallized from methanol-ethyl acetate; m.p. 228° C. (decom.); $^1$H NMR (DMSO-d$_6$): δ 2.52 (m, 1H, H2'), 3.30–3.55 (m, 3H, H5', H4a"), 3.69 (dd, J=11.1 Hz, 2.7 Hz, 1H, H2a"), 3.73 (d, J=10.8 Hz, H4b"), 4.05 (d, J=10.8 Hz, 1H, H2b"), 4.40 (m, 1H, H2b"), 5.03 (t, J=6.0 Hz, 1H, OH), 5.74 (d, J=4.2 Hz, 1H, OH), 6.24 (s, 1H, H1'), 8.06 (s, 1H, H8), 8.30 (s, 1H, H2), 12.40 (s, 1H, NH); MS m/z 295 (MH$^+$).

Example 21

Preparation of (1S,3S,4R,8S)-8-hydroxy-1-hydroxymethyl-3-(hypoxanthin-9-yl)-2,6-dioxabicyclo[3,2,1]octane (21)

To a solution of (1R,3S,4R,8S)-1-acetoxymethyl-8-benzyloxy-3-(6-chloropurin-9-yl)-2,6-dioxabicyclo[3,2,1] octane (120 mg, 0.27 mmol), mercaptoethanol (0.15 mL, 2.1 mmol) in methanol (16 mL) was added sodium methoxide (1.62 mmol, 0.30 mL of 5.4 M in methanol). The similar procedure as described for Example 20 gave 37 mg (47%) of the titled compound as a hygroscopic solid; $^1$H NMR (DMSO-d$_6$) δ 2.52 (m, 1H, H2'), 3.06 (dd, J=11.7 Hz, 2.4 Hz, 1H, H2a"), 3.34–3.53 (m, 2H, H5'), 3.56 (d, J=11.1 Hz, 1H, H4a"), 3.79 (d, J=11.4 Hz, 1H, H4b"), 3.98 (d, J=11.4 Hz, 1H, H2b"), 4.31 (d, J=4.5 Hz, 1H, H3'), 4.89 (br, 1H, OH), 5.99 (br, 1H, OH), 6.28 (d, J=4.2 Hz, 1H, H1'), 8.03 (s, 1H, H8), 8.27 (s, 1H, H2), 12.30 (br, 1H, NH).

Example 22

Preparation of (1S,3S,4R,8S)-3-(guanin-9-yl)-8-hydroxy-1-hydroxymethyl-2,6-dioxabicyclo[3,2,1]octane (23)

A similar procedure as described for Example 18 gave the titled compound (41 mg, 66%) as an off-white solid from (1R,3S,4R,8S)-1-acetoxymethyl-3-(N$^2$-acetylguanin-9-yl)-8-benzyloxy-2,6-dioxabicyclo[3,2,1]octane (100 mg). $^1$H NMR (DMSO-d$_6$+D$_2$O ) δ 2.42 (m, 1H, H2'), 3.15 (dd, J=11.4 Hz, 2.1 Hz, 1H, H2a"), 3.34 (d, J=11.4 Hz, 1H, H5a'), 3.47 (d, J=12.6 Hz, 1H, H5b'), 3.51 (d, J=12.0 Hz, 1H, H4a"), 3.77 (d, J=10.8 Hz, 1H, H4b"), 3.98 (d, J=11.7 Hz, 1H, H2b"), 4.23 (d, J=4.8 Hz, 1H, H3'), 4.80 (br, 1H, OH), 5.90 (br, 1H, OH), 6.05 (d, J=4.2 Hz, 1H, H1'), 6.52 (br, 2H, NH$_2$), 7.93 (s, 1H, H8), 12.30 (br, 1H, NH); MS m/z 310 (MH$^+$).

Example 23

Preparation of (1R,3R,4R,8S)-1-acetoxymethyl-8-benzyloxy-3-(thymin-1-yl)-2,6-dioxabicyclo[3,2,1] octane (24)

The reaction followed the same procedure as described for Example 14 except that the coupling reagent was tin (IV) chloride (0.45 mL) and the sugar substrate was (1R,3S,4R,8S)-1-acetoxymethyl-8-benzyloxy-3-methoxy-2,6-dioxabicyclo[3,2,1]octane (202 mg, 0.63 mmol). Chromatography on silica with 5% EtOH in CH$_2$Cl$_2$ gave a mixture (233 mg, 89%) of the titled compound (β-anomer) and its α-anomer (ratio of β:α, ~4:1) as a colorless solid. $^1$H NMR (CDCl$_3$) of the β-anomer (from the spectrum of a mixture of the α- and β-anomers) δ 1.93 (d, J=0.9 Hz, 1H, ArCH$_3$), 2.05 (s, 3H, OAc), 2.66 (m, 1H, H2'), 3.48 (d, J=11.1 Hz, H4a"), 3.86–4.12 (m, 5H, H2a", H2b", H3', H4b", H5a'), 4.26 (d, J=12.6 Hz, H5b'), 4.44, 4.64 (AB, J=11.4 Hz, 2H, Bn), 6.06 (s, 1H, H1'), 7.26–7.42 (m, 5H, Bn), 7.59 (d, J=1.2 Hz, 1H, H6), 8.94 (s, 1H, NH).

Example 24

Preparation of (1R,3R,4R,8S)-1-acetoxymethyl-8-benzyloxy-3-(uracil-1-yl)-2,6-dioxabicyclo[3,2,1] octane (25)

A similar procedure as described for Example 23 gave, after chromatography on silica with 5% EtOH in methylene chloride, a mixture (267 mg, 87%) of the titled compound and its α-anomer (ratio of β:α, ~9:1) as a colorless solid from (1R,3S,4R,8S)-1-acetoxymethyl-8-benzyloxy-3-methoxy-2,6-dioxabicyclo[3,2,1]octane (230 mg, 0.71 mmol) and silylated uracil (2.0 mmol). The titled compound (β-anomer) was partially separated by chromatography on silica; m.p. 145–147° C. (EtOAc-hexanes); $^1$H NMR (CDCl$_3$) δ 2.02 (s, 3H, OAc), 2.67 (m, 1H, H2'), 3.49 (d, J=11.4 Hz, 1H, H4a"), 3.86–3.97 (m, 3H, H2a", H3', H4b"), 4.08 (d, J=12.3 Hz, 1H, H5a'), 4.09 (d, J=10.5 Hz, 1H, H2b"), 4.25 (d, J=12.3 Hz, 1H, H5b'), 4.44, 4.64 (AB, J=11.7 Hz, 2H, Bn), 6.05 (s, 1H, H1'), 7.26–7.40 (m, 5H, Bn), 5.69 (d, J=8.1 Hz, 1H, H5), 7.79 (d, J=8.4 Hz, 1H, H6), 8.92 (s, 1H, NH); Anal. Calcd. for C$_{20}$H$_{22}$N$_2$O$_7$: C, 59.69; H, 5.51; N, 6.96. Found: C, 59.45; H, 5.56; N, 6.91.

Example 25

Preparation of (1R,3R,4R,8S)-1-acetoxymethyl-8-benzyloxy-3-(N$^4$-benzoylcytosin-1-yl)-2,6-dioxabicyclo[3,2,1 ]octane (26)

A similar procedure as described for Example 23 gave, after chromatography on silica with 5% EtOH in methylene chloride, 910 mg (90%) of the titled compound (β-anomer) as a colorless solid from the reaction of (1R,3S,4R,8S)-1-acetoxymethyl-8-benzyloxy-3-methoxy-2,6-dioxabicyclo[3,2,1]octane (645 mg, 2.0 mmol) with silylated N[4]-benzoylcytosine (4.0 mmol); m.p. 173–174° C. (EtOAc); $^1$H NMR (CDCl$_3$) δ 2.07 (s, 3H, OAc), 2.83 (m, 1H, H2'), 3.51 (d, J=11.1 Hz, H4a"), 3.86 (d, J=5.4 Hz, 1H, H3'), 3.97 (d, J=11.1 Hz, 1H, H4b"), 3.99–4.13 (m, 3H, H2a", H2b", H5a'), 4.27 (d, J=12.3 Hz, 1H, H5b'). 4.38, 4.61 (AB, J=11.4 Hz, 2H, Bn), 6.15 (s, 1H, H1'), 7.24–7.38 (m, 5H, Bn), 7.50–7.66 (m, 4H, H5, Bz), 7.90 (m, 2H, Bz), 8.28 (d, J=7.5 Hz, 1H, H6), 8.84 (br, 1H, NH); Anal. Calcd. for C$_{27}$H$_{27}$N$_3$O$_7$: C, 64.15; H, 5.38; N, 8.31. Found: C, 64.10; H, 5.20; N, 8.43.

Example 26

Preparation of (1S,3R,4R,8S)-8-hydroxy-1-hydroxymethyl-3-(thymin-1-yl)-2,6-dioxabicyclo[3,2,1]octane (27)

To a solution of the mixture of (1R,3R,4R,8S)-1-acetoxymethyl-8-benzyloxy-3-(thymin 1-yl)-2,6-dioxabicyclo[3,2,1]octane and its α-anomer (~4:1, 200 mg, 0.48 mmol) in anhydrous methylene chloride (4 mL) at 0° C. was added boron trichloride (1.0 M in CH$_2$CH$_2$, 8 mL). The resulting reaction mixture was stirred at room temperature for 8 h, at 15° C. overnight, and then cooled to 0° C. Methanol (5.0 mL) was added dropwise, followed by addition of 1.0 M NaOMe in MeOH until pH 8. The solution was separated and the precipitate extracted with 20% methanol in methylene chloride thoroughly. The combined filtrate was dried (Na$_2$SO$_4$), and concentrated to dryness. Chromatography on silica with 10–15% methanol in ethyl acetate gave the titled compound (78 mg), a mixture of the titled compound and its α-anomer (24 mg), and the α-anomer (23 mg), all as a colorless solid. Total yield was 91%. Crystallization of the titled compound from methanol-ethyl acetate gave the crystalline solid; m.p. 217–218° C.; $^1$H NMR (DMSO-d$_6$): δ 1.75 (d, J=1.2 Hz, 1H, ArCH$_3$), 2.24 (m, 1H, H2'), 3.20 (d, J=10.8 Hz, 1H, H4a"), 3.33–3.58 (m, 3H, H2a", H5'), 3.66 (d, J=10.8 Hz, H4b"), 3.97 (d, J=10.5 Hz, 1H, H2b"), 4.14 (m, 1H, H3'), 5.24 (t, J=5.1 Hz, 1H, OH), 5.67 (d, J=2.4 Hz, 1H, OH), 5.82 (s, 1H, H1'), 7.95 (d, J=0.9 Hz, 1H, H6), 11.32 (s 1H, NH); MS m/z 285 (MH$^+$); Anal. Calcd. for C$_{12}$H$_{16}$N$_2$O$_6$: C, 50.70; H, 5.67; N, 9.85. Found: C, 50.65; H, 5.57; N, 9.73.

Example 27

Preparation of (1S,3R,4R,8S)-8-hydroxy-1-hydroxymethyl-3-(uracil-1-yl)-2,6-dioxabicyclo[3,2,1]octane (28)

A similar procedure as described for Example 26 gave, after chromatography on silica with 10% methanol in methylene chloride, 110 mg (76%) of the titled compound as a white solid from (1R,3R,4R,8S)-1-acetoxymethyl-8-benzyloxy-3-(uracil-1-yl)-2,6-dioxabicyclo[3,2,1]-octane (215 mg, 0.53 mmol). The titled compound was contaminated by a small amount of its α-anomer. The pure, titled compound was obtained by recrystallization from acetone-ethyl acetate; m.p. 218–219° C.; $^1$H NMR (acetone-d$_6$) δ 2.42 (m, 1H, H2'), 3.27 (d, J=10.8 Hz, 1H, H4a"), 3.58–3.72 (m, 3H, H2a", H5'), 3.83 (d, J=10.8 Hz, 1H, H4b"), 4.13 (d, J=10.5 Hz, 1H, HH2b"), 4.37 (t, J=5.1 Hz, 1H, OH), 4.42 (m, 1H, H3'), 4.88 (d, J=3.9 Hz, 1H, OH), 5.52 (d, J=7.8 Hz, 1H, H5), 5.95 (s, 1H, H1'), 8.17 (d, J=7.8 Hz, 1H, H6), 10.02 (s, 1H, NH); MS m/z 271 (MH$^+$); Anal. Calcd. for C$_{11}$H$_{14}$N$_2$O$_6$: C, 48.89; H, 5.22; N, 10.37. Found: C, 48.60; H, 5.64; N, 10.21.

Example 28

Preparation of (1S,3R,4R,8S)-3-(cytosin-1-yl)-8-hydroxy-1-hydroxymethyl-2,6-dioxabicyclo[3,2,1]octane (30)

A similar procedure as described for Example 26 gave, after chromatography on silica with 10% MeOH in methylene chloride from (1R,3R,4R,8S)-1-acetoxymethyl-8-benzyloxy-3-(N[4]-benzoylcytosin-1-yl)-2,6-dioxabicyclo-[3 2,1]octane, 364 mg (65%) of (1S,3R,4R,8S)-3-(N[4]-benzoylcytosin-1-yl)-8-hydroxy-1-hydroxymnethyl-2,6-dioxabicyclo-[3,2,1]octane (760 mg), 120 mg (0.32 mmol) of which was dissolved in a saturated solution of ammonia in methanol and the solution stirred at room temperature for 24 h. Ammonia and methanol were evaporated and the residue was dissolved in water, followed by thorough extraction with chloroform (5 times) and then with toluene (2 times). Water was evaporated and crystallization from methanol gave 62 mg of the titled compound (45 mg of crystalline solid and 17 mg of non-crystalline solid); m.p. 250° C. (decom.); $^1$H NMR (CD$_3$OD) δ 2.33 (m, 1H, H2'), 3.31 (d, J=11.1 Hz, 1H, H4a"), 3.57 (d, J=12.3 Hz, 1H, H5a'), 3.65 (d, J=12.3 Hz, 1H, H5b'), 3.78 (dd, J=10.5 Hz, 2.7 Hz, H2a"), 3.84 (d, J=11.1 Hz, 1H, H4b"), 4.14 (d, J=10.5 Hz, 1H, H2b"), 4.20 (d, J=5.1 Hz, 1H, H3'), 5.86 (d, J=7.5 Hz, 1H, H5), 5.96 (s, 1H, H1'), 8.22 (d, J=7.8 Hz, 1H, H6); MS: m/z 270 (MH$^+$); Anal. Calcd. for C$_{11}$H$_{15}$N$_3$O$_5$: C, 49.07; H, 5.62; N, 15.61. Found: C, 48.93; H. 5.55; N, 15.64.

Similarly, (1S,3R,4R,8S)-3-(N[4]-acetylcytosin-1-yl)-8-hydroxy-1-hydroxymethyl-2,6-dioxabicyclo-[3,2,1]octane was prepared.

An alternative method. A mixture of (1S,3R,4R,8S)-8-hydroxy-1-hydroxymethyl-3-uracil-1-yl)-2,6-dioxabicyclo [3,2,1]octane (170 mg, 0.63 mmol), acetic anhydride (2.16 mL, 0.1 mmol), and pyridine (0.29 mL, 3.5 mmol) in anhydrous DMF (2.5 mL) was stirred at room temperature overnight, diluted with methylene chloride, washed with brine and 10% NaHCO$_3$, dried (Na$_2$SO$_4$), concentrated to dryness. Chromatography on silica with ethyl acetate-hexanes (2:1) gave 117 mg (77%) of the 3',5'-diacetyl derivative of(1S,3R,4R,8S)-8-acetoxy-1-caetoxymethyl-3-(uracil-1-yl)-2,6-dioxabicyclo[3,2,1]-octane.

The (1S,3R,4R,8S)-8-acetoxy-1-caetoxymethyl-3-(uracil-1-yl)-2,6-dioxabicyclo-[3,2,1]octane (175 mg, 0.58 mmol) was dissolved in anhydrous pyridine (1.5 mL) and the resulting solution cooled to 0° C. under argon, followed by addition of 4-chlorophenyl dichlorophosphate (0.29 mL, 1.75 mmol). The resulting solution was warmed up to room temperature and transferred to a septum-capped vial containing 1,2,4-triazole (120 mg, 1.75 mmol). The reaction mixture was stirred at room temperature for 3 days, diluted with CH$_2$Cl$_2$, washed with brine and 5% NaHCO$_3$, dried (Na$_2$SO$_4$), and concentrated to dryness. The residue was dissolved in dioxane (7 mL) and 30% ammonium hydroxide (10 mL). The solution stood at room temperature for 16 h and the solvents were evaporated. The residue was chromatographed on silica with Et$_3$N-MeOH-CHCl$_3$ (5:30:65) to give 74 mg (55%) of the titled compound as a slightly yellow solid.

Example 29

Preparation of (1R,3R,4R,8S)-1-acetoxymethyl-3-(N[2]-acetylguanin-7-yl)-8-benzyloxy-2,6-dioxabicyclo[3,2,1]-octane (31)

The silylated base from N[2]-acetylguanine (386 mg, 2.0 mmol) was prepared according to the procedure described for Example 17 and dissolved in a solution of (1R,3S,4R, 8S)-1-acetoxymethyl-8-benzyloxy-3-methoxy-2,6-dioxabicyclo[3,2,1]octane (477 mg, 1.48 mmol) in anhydrous 1,2-dichloroethane (10 mL), followed by addition of tin (IV) chloride (0.75 mL) in 1,2-dichloroethane (2.0 mL). The resulting mixture was heated at reflux for 3 h, then at 70° C. overnight, and cooled to 0° C. The mixture was neutralized with 2.0 M sodium carbonate, filtered through celite, and thoroughly extracted with chloroform. The combined filtrate was dried (Na$_2$SO$_4$) and concentrated to dryness. Chromatography on silica with 5% EtOH in chloroform gave 297 mg (42%) of the titled compound, 73 mg (10%) of the N9-coupled β-anomer of the titled compound, and 46 mg (6%) of the N9-coupled α-anomer, all as a white solid. The titled compoun: m.p. 176–178° C. (CH$_3$Cl-EtOAc); $^1$H NMR (CDCl$_3$) δ 2.09 (s, 3H, OAc), 2.40 (s, 3H, NAc), 2.78 (m, 1H, H2'), 3.53 (d, J=11.4 Hz, 1H, H4a"), 3.99 (d, J=11.1 Hz, H4b"), 4.03–4.18 (m, 4H, H2a", H2b", H3', H5a'), 4.26 (d, J=12.6 Hz, 1H, H5b'), 4.39, 4.58 (AB, J=11.7 Hz, 2H, Bn), 6.62 (s, 1H, H1'), 7.22–7.40 (m, 5H, Bn), 8.21 (s, 1H, H8), 10.60 (s, 1H, NH), 12.34 (s, 1H, NH); Anal. Calcd. for C$_{23}$H$_{251}$N$_5$O$_8$: C, 55.31; H, 5.05; N, 14.02. Found: C, 55.35; H, 4.83; N, 13.80.

Example 30

Preparation of (1R,3R,4R,8S)-1-acetoxymethyl-3-(N$^2$-acetylguanin-9-yl)-8-benzyloxy- 2,6-dioxabicyclo[3,2,1]-octane (32)

The same amount of the silylated N$^2$-acetylguanine as described for Example 29 was dissolved in a solution of (1R,3R,4R,8S)-1-acetoxymethyl-3-(N$^2$-acetylguanin-7-yl)-8-benzyloxy-2,6-dioxabicyclo[3,2,1]-octane (370 mg, 0.76 mmol) in anhydrous 1,2-dicloroethane (10 mL) and trimethylsilyl triflate (0.54 mL, 3.0 mmol) in 1,2-dichloroethane (3 mL) was added. The resulting solution was heated under reflux overnight. Additional TMSOTf (0.54 mL) was added and the mixture refluxed for additional two days. The same work-up as described for Example 29 gave, after chromatography on silica with 5°% ethanol in chloroform, 104 mg (28%) of the intact starting material, 91 mg (25%) of the titled compound, and 80 mg (22%) of the α-anomer of the titled compound, all as a white solid. The titled compound: m.p. 128–131° C. (CH$_3$Cl-EtOAc); $^1$H NMR (CDCl$_3$) δ 2.02 (s, 3H, OAc), 2.30 (s, 3H, NAc), 2.67 (m, 1H, H2'), 3.50 (d, J=10.8 Hz, 1H, H4a"), 3.78 (dd, J=10.8 Hz, 2.7 Hz, 1H, H2a"), 3.99 (d, J=10.8 Hz, H4b"), 4.12 (d, J=12.3 Hz, 1H, H5a'), 4.14 (d, J=10.8 Hz, 1H, H2b"), 4.27 (d, J=12.3 Hz, 1H, H5b'), 4.33 (d, J=5.1 Hz, 1H, H3'), 4.49, 4.62 (AB, J=11.7 Hz, 2H, Bn), 6.25 (s, 1H, H1'), 7.26–7.38 (m, 5H, Bn), 7.83 (s, 1H, H8), 9.0 (s, 1H, NH), 11.95 (s, 1H, NH); MS: m/z 310 (MH$^+$); Anal. Calcd. for C$_{23}$H$_{25}$N$_5$O$_8$: C, 55.31; H, 5.05; N, 14.02. Found: C, 55.70; H, 5.00; N, 13.95.

Example 31

Preparation of (1S,3R,4R,8S)-3-(guanin-9-yl)-8-hydroxy-1-hydroxymethyl-2,6-dioxabicyclo[3,2,1] octane (33)

A similar procedure as described for Example 22 gave, after chromatography, 52 mg (45%) of the titled compound as a colorless solid from (1R,3R,4R,8S)-1-acetoxymethyl-3-(N$^2$-acetylguanin-9-yl)-8-benzyloxy-2,6-dioxabicyclo[3, 2,1]-octane (180 mg). Crystallization from water-ethanol (9:1) gave a crystalline solid; m.p. 258° C. (decom.); $^1$H NMR (DMSO): δ 2.45 (m, 1H, H2'), 3.31 (d, J=10.8 Hz, 1H, H4a"), 3.36–3.50 (m, 2H, H5a', H5b'), 3.60 (dd, J=10.2 Hz, 2.7 Hz, 1H, H2a"), 3.1 (d, J=11.1 Hz, H4b"), 4.03 (d, J=10.5 Hz, 1H, H2b"), 4.36 (m, 1H, H3'), 4.95 (t, J=5.7 Hz, 1H, OH), 5.70 (d, J=3.9 Hz, 1H, OH), 6.06 (s, 1H, H1'), 6.55 (br, 2NH$_2$), 7.90 (s, 1H, H8), 10.68 (s, 1H, NH); MS m/z 310 (MH$^+$).

Example 32

Preparation of (1S,3R,4R,8S)-8-hydroxy-1-(4,4'-dimethoxytrityloxymethyl)-3-(N$^4$-acetylcytosin-yl)-2,6-dioxabicyclo[3,2,1]octane (35)

A solution of (1S,3R,4R,8S)-8-hydroxy-1-hydroxymethyl-3-(N$^4$-acetylcytosin-yl)-2,6-dioxabicyclo[3, 2,1]octane (200 mg, 0.64 mmol) and 4,4'-dimethoxytrityl chloride (548 mg, 0.61 mmol) in anhydrous pyridine (7 mL) stood at room temperature overnight, diluted with ethyl acetate, washed with brine and 10% NaHCO$_3$, dried over sodium sulfate, and concentrated. Chromatography on silica with 10% ethanol in chloroform gave 342 mg (87%) of the titled compound as colorless foam.

Similarly, (1S,3R,4R,8S)-8-hydroxy-1-(4,4'-dimethoxytrityloxymethyl)-3-(N$^4$-benzoyl-cytosin-1-yl)-2, 6-dioxabicyclo[3,2,1]octane (36) and (1S,3R,4R,8S)-8-hydroxy-1-(4,4'-dimethoxytrityloxymethyl)-3-(thymrin-yl)-2,6-dioxabicyclo[3,2,1]octane (34) were prepared.

Example 33

Preparation of (1S,3R,4R,8S)-8-hydroxy-1-(4,4'-dimethoxytrityloxymethyl)-3-(N$^4$-acetylcytosin-yl)-2,6-dioxabicyclo[3,2,1]octane 8-O-(2-cyanoethyl-N, N-diisopropylphophoramidite) (38)

To a stirred solution of (1S,3R,4R,8S)-8-hydroxy-1-(4,4'-dimethoxytrityloxy-methyl)-3-(N$^4$-acetyl-cytosin-yl)-2,6-dioxabicyclo[3,2,1]octane (320 mg, 0.52 mmol) and diisopropylethyl-amine (0.36 mL, 2.08 mmol) in anhydrous dichloromethane (6 mL) at 0° C. under argon was added dropwise 2-cyanoethyl-N,N-diisopropylchlorophosphoramidite (0.23 mL, 1.04 mmol). The resulting solution was stirred at ambient temperature for 4 h, cooled with ice, diluted with ethyl acetate, washed with cold 10% NaHCO$_3$, dried over sodium sulfate, and concentrated at room temperature. Chromatography on silica with 5% triethylamine and 5% acetone in methylene chloride gave 376 mg (89%) of the titled compound as a colorless foam.

Similarly, (1S,3R,4R,8S)-8-hydroxy-1-(4,4'-dimethoxytrityloxymethyl)-3-(N$^4$-benzoyl-cytosin-1-yl)-2, 6-dioxabicyclo[3,2,1]octane 8-O-(2-cyanoethyl-N,N-diisopropyl-phophoramidite) (39) and (1S,3R,4R,8S)-8-hydroxy-1-(4,4'-dimethoxytrityloxymethyl)-3-(thymin-1-yl)-2,6-dioxabicyclo[3,2,1]octane 8-O-(2-cyanoethyl-N,N-diisopropyl-phophoramidite) (37) were prepared.

Example 34

Preparation of Oligonucleotides Containing 2,4-Bicyclonucleotides

This example illustrates the use of bicyclonucleoside phosphoramidites 37–39 for the synthesis of oligonucleotide containing the 2'-C,4'-C-bridged bicyclonucleosides. The oligonuceotides in this example were synthesized by using phosphoramidite approach. The modified oligonuceotides were synthesized by a standard procedure (a protocol for ABI 394 Synthesizer from Perkin-Elmer, 1994) except that a more concentrated solution and a prolonged coupling time were used. The solution for the modified phosphoramidites were 0.13 M that is 30% more concentrated than those for the unmodified phosphoramidites (0.1 M). Ten minutes coupling time was used for the modified phosphoramidites and five minutes for the unmodified phosphoramidites next to the modified ones. The coupling yields for the modified phosphoramidites are comparable to the unmodified (98–99%). The modified ODNs were purified by reverse-phase HPLC and characterized by mass spectrometry.

The following synthesized sequences are listed as examples.

5'-d(ATCTCTCCGCTTCCTTTC)-3'
5'-d(ATCTCTCCGCTTCCTTTC)-3'

5'-d(ATCTCTCCGCTTCCTTTC)-3'

5'-d(ATCTCTCCGCTTCCTTTC)-3'

5'-d(ATCTCTCCGCTTCCTTTC)-3'

5'-d(CTTCCTGTCTGATGGCTTC)-3'

5'-d(CTTCCTGTCTGATGGCTTC)-3'

5'-d(CTTCCTGTCTGATGGCTTC)-3'

5'-d(CTTCCTGTCTGATGGCTTC)-3'

5'-d(CTTCCTGTCTGATGGCTTC)-3'

5'-d(CTTCCTGTCTGATGGCTTC)-3'

A, C, G, and T=unmodified deoxyribonucleoside

T=2',4'-C-bridged thymidine

C=2',4'-C-bridged deoxycytidine

Example 35

Hybridization Properties of Oligonucleotides Containing the 2'-C,4'-C-bridged Bicyclonucleotides Hybridization of the modified oligonucleotides to the complementary DNA and RNA was studied through the thermodynamic melting measurements (Wang et al. *Nucleosides Nucleotides* 1997, 16, 445). As can be seen in Table 1, the modifications enhance hybridization to RNA significantly. For the sequences containing, the bicyclic thymidine T, the increases in Tm values are in the range of 2.2–3.3 degrees per modification. The sequences containing the bicyclic cytidine C also have higher Tm values than the unmodified oligonucleotides, 2.4° higher per modification for Sequence 4 and 1.9° higher per modification for Sequence 5. Sequence 12 contains a mismatched nucleoside (G in the middle of the sequence is replaced by T) have a Tm value eleven degree lower than Sequence 10, which reveals the sequence specifity. For the sequences in which all the T and C are replaced by T and C, the Tm values (>90°) were increased further so that it was not possible to obtain the accurate values in the measurement system.

TABLE 1

Hybridization data of oligonucleotides containing the 2'-C,4'-C-bridged bicyclonucleotides

| Sequence | Tm ° C. RNA | ΔTm ° C./Mod. |
|---|---|---|
| 1. 5'-d(ATCTCTCCGCTTCCTTTC)-3' | 64.4 | |
| 2. 5'-d(ATCTCTCCGCTTCCTTTC)-3' | 78.1 | +2.8 |
| 3. 5'-d(ATCTCTCCGCTTCCTTTC)-3' | ~82 | +2.2 |
| 4. 5'-d(ATCTCTCCGCTTCCTTTC)-3' | 71.7 | +2.4 |
| 5. 5'-d(ATCTCTCCGCTTCCTTTC)-3' | 77.5 | +1.9 |
| 6. 5'-d(ATCTCTCCGCTTCCTTTC)-3' | >90 | |
| 7. 5'-d(CTTCCTGTCTGATGGCTTC)-3' | 63.0 | |
| 8. 5'-d(CTTCCTGTCTGATGGCTTC)-3' | 69.5 | +3.3 |
| 9. 5'-d(CTTCCTGTCTGATGGCTTC)-3' | 76.2 | +3.3 |
| 10. 5'-d(CTTCCTGTCTGATGGCTTC)-3' | 81.4 | +2.3 |
| 11. 5'-d(CTTCCTGTCTGATGGCTTC)-3' | >90 | |
| 12. 5'-d(CTTCCTGTCTTATGGCTTC)-3' | 70.3 | |

T = 2',4'-*C*-bridged thymidine, C = 2',4'-*C*-bridged cytidine. The samples for Tm measurements contain 2.0 μM of modified oligonucleotides and 2.0 μM of either complementary DNA or RNA in a buffer (10 mM sodium phosphate, 0.1 mM EDTA, and 0.1 M sodium chloride, pH 7.0).

Thus, specific embodiments and applications of displays and methods for producing novel nucleosides and oligonucleotides with bicyclic sugar moieties have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A compound having the following formula:

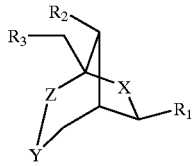

wherein X is O or $CH_2$, Y is O, and Z is $CH_2$;

$R_1$ is selected from the group consisting of adenine, cytosine, guanine, hypoxanthine, uracil, thymine, and a heterocycle wherein the heterocycle is selected from the group consisting of a substituted 1,3-diazine, unsubstituted 1,3-diazine, and an unsubstituted 7H imidazo[4,5]1,3 diazine; and $R_2$, $R_3$ are independently selected from a group consisting of H, OH, DMTO, TBDMSO, BnO, THPO, AcO, BzO, $OP(NiPr_2)O(CH_2)_2CN$, $OPO_3H$, diphosphate, and triphosphate, wherein $R_2$ and $R_3$ together may be $PhCHO_2$, $TIPDSO_2$ or $DTBSO_2$.

2. A compound according to claim 1, where X is oxygen; Y is O, and Z is methylene.

3. An oligonucleotide comprising at least one monomer according to claim 1.

4. An oligonucleotide comprising at least one monomer according to claim 2.

5. A pharmaceutical composition comprising:
   a compound according to claim 1 and a pharmaceutically acceptable carrier, wherein the compound is present in an amount effective to exhibit antiviral activity.

6. The pharmaceutical composition of claim 5 wherein the compound is present in an amount effective to exhibit antiviral activity against an HIV virus and an HBV virus.

7. The pharmaceutical composition of claim 5 wherein the compound is present in an amount effective to exhibit antiviral activity against an HIV virus.

8. The pharmaceutical composition of claim 5 wherein the compound is present in an amount effective to exhibit antiviral activity against an HBV virus.

* * * * *